United States Patent
Spiegelman et al.

(10) Patent No.: US 10,994,254 B2
(45) Date of Patent: May 4, 2021

(54) SYSTEM, DEVICE, AND METHOD FOR CONTROLLING MASS FLOW OF A CATALYTICALLY REACTIVE GAS IN A MIXED GAS STREAM

(71) Applicant: RASIRC, Inc., San Diego, CA (US)

(72) Inventors: Jeffrey J. Spiegelman, San Diego, CA (US); Russell Holmes, San Diego, CA (US); Christopher Ramos, Bonita, CA (US)

(73) Assignee: RASIRC, Inc., San Diego, CA (US)

( * ) Notice: Subject to any disclaimer, the term of this patent is extended or adjusted under 35 U.S.C. 154(b) by 59 days.

(21) Appl. No.: 16/494,448

(22) PCT Filed: Mar. 15, 2018

(86) PCT No.: PCT/US2018/022686
§ 371 (c)(1),
(2) Date: Sep. 16, 2019

(87) PCT Pub. No.: WO2018/170292
PCT Pub. Date: Sep. 20, 2018

(65) Prior Publication Data
US 2020/0086287 A1    Mar. 19, 2020

Related U.S. Application Data

(60) Provisional application No. 62/472,711, filed on Mar. 17, 2017, provisional application No. 62/552,305, filed on Aug. 30, 2017.

(51) Int. Cl.
*B01J 4/00* (2006.01)
*B01J 8/00* (2006.01)
(Continued)

(52) U.S. Cl.
CPC ............ *B01J 4/008* (2013.01); *B01J 8/001* (2013.01); *B01J 19/0013* (2013.01); *A61L 2/208* (2013.01);
(Continued)

(58) Field of Classification Search
CPC ..... A61L 2/00; A61L 2/16; A61L 2/20; A61L 2/208; A61L 2/24; B01J 4/00;
(Continued)

(56) References Cited

U.S. PATENT DOCUMENTS

| | | | |
|---|---|---|---|
| 4,436,674 A | 3/1984 | McMenamin | |
| 5,167,927 A | 12/1992 | Karlson | |

(Continued)

FOREIGN PATENT DOCUMENTS

| | | | |
|---|---|---|---|
| WO | 1991/005998 A1 | 5/1991 | |
| WO | 2006/117328 A1 | 11/2006 | |

(Continued)

OTHER PUBLICATIONS

PCT/US2018/022686 International Search Report and Written Opinion dated Jun. 7, 2018.
(Continued)

*Primary Examiner* — Natasha E Young
(74) *Attorney, Agent, or Firm* — Wagenknecht IP Law Group PC

(57) ABSTRACT

Provided herein are methods, systems, and apparatus for measuring and/or controlling mass flow/concentration of a catalytically reactive gas within a mixed gas stream by determining thermal rise due to decomposition.

31 Claims, 14 Drawing Sheets

(51) Int. Cl.
*B01J 19/00* (2006.01)
*A61L 2/20* (2006.01)
*A61L 2/24* (2006.01)

(52) U.S. Cl.
CPC ........ *A61L 2/24* (2013.01); *B01J 2219/00164* (2013.01)

(58) Field of Classification Search
CPC ..... B01J 4/008; B01J 8/00; B01J 8/001; B01J 19/00; B01J 19/0006; B01J 19/0013; B01J 37/00; B01J 37/02; B01J 37/0215; B01J 2219/00; B01J 2219/00049; B01J 2219/00164
See application file for complete search history.

(56) References Cited

U.S. PATENT DOCUMENTS

| | | |
|---|---|---|
| 5,600,142 A | 2/1997 | Van Den Berg et al. |
| 5,608,156 A | 3/1997 | Ando et al. |
| 6,491,881 B2 | 12/2002 | Fryer et al. |
| 6,953,549 B2 * | 10/2005 | Hill .................... A61L 2/208 422/292 |
| 2002/0139124 A1 | 10/2002 | Palermo |
| 2006/0088441 A1 | 4/2006 | Hill |
| 2012/0298207 A1 | 11/2012 | Woelk et al. |
| 2013/0233170 A1 | 9/2013 | Spiegelman et al. |

FOREIGN PATENT DOCUMENTS

| | | |
|---|---|---|
| WO | 2013/148262 A1 | 10/2013 |
| WO | 2016/065132 A1 | 4/2016 |

OTHER PUBLICATIONS

Schumb et al. "Hydrogen Peroxide," 1955, 228-229, Reinhold Publishing Corporation, New York.

* cited by examiner

SYSTEM, DEVICE, AND METHOD FOR CONTROLLING MASS FLOW OF A CATALYTICALLY REACTIVE GAS IN A MIXED GAS STREAM

CROSS REFERENCE TO RELATED APPLICATION(S)

This application is a US national phase application under 35 U.S.C. § 371 of International Patent Application No. PCT/US2018/022686, now WO 2018/170292, filed Mar. 15, 2018, which claims the benefit of priority under 35 U.S.C. § 119(e) of U.S. Ser. No. 62/472,711, filed Mar. 17, 2017, and of U.S. Ser. No. 62/552,305, filed Aug. 30, 2017, the entire content of each of which is incorporated herein by reference.

BACKGROUND OF THE INVENTION

Field of the Invention

The invention relates generally to combustible gases and more specifically to methods, systems, and devices for measuring concentration of a combustible and/or catalytically reactive gas within a mixed gas stream due to thermal rise.

Background Information

Various process gases may be used in the manufacturing and processing of micro-electronics. In addition, a variety of chemicals may be used in other environments demanding high purity gases, e.g., critical processes, including without limitation microelectronics applications, wafer cleaning, wafer bonding, photoresist stripping, silicon oxidation, surface passivation, photolithography mask cleaning, atomic layer deposition, chemical vapor deposition, flat panel displays, flexible displays, solar cells, disinfection of surfaces contaminated with bacteria, viruses and other biological agents, industrial parts cleaning, pharmaceutical manufacturing, production of nano-materials, power generation and control devices, fuel cells, power transmission devices, and other applications in which process control and purity are critical considerations. In those processes, it is necessary to deliver specific amounts of certain process gases under controlled operating conditions, e.g., temperature, pressure, and flow rate.

For a variety of reasons, gas phase delivery of process chemicals is preferred to liquid phase delivery. For applications requiring low mass flow for process chemicals, liquid delivery of process chemicals is not accurate or clean enough. Gaseous delivery would be desired from a standpoint of ease of delivery, accuracy and purity. Gas flow devices are better attuned to precise control than liquid delivery devices. Additionally, micro-electronics applications and other critical processes typically have extensive gas handling systems that make gaseous delivery considerably easier than liquid delivery. One approach is to vaporize the process chemical component directly at or near the point of use. Vaporizing liquids provides a process that leaves heavy contaminants behind, thus purifying the process chemical. However, for safety, handling, stability, and/or purity reasons, many process gases are not amenable to direct vaporization.

There are numerous process gases used in micro-electronics applications and other critical processes. Ozone is a gas that is typically used to clean the surface of semiconductors (e.g., photoresist stripping) and as an oxidizing agent (e.g., forming oxide or hydroxide layers). One advantage of using ozone gas in micro-electronics applications and other critical processes, as opposed to prior liquid-based approaches, is that gases are able to access high aspect ratio features on a surface. For example, according to the International Technology Roadmap for Semiconductors (ITRS), current semiconductor processes should be compatible with a half-pitch as small as 7 nm. The next technology node for semiconductors is expected to have a half-pitch of 5-7 nm, and the ITRS calls for <5 nm half-pitch in the near future. At these dimensions, liquid-based chemical processing is not feasible because the surface tension of the process liquid prevents it from accessing the bottom of deep holes or channels and the corners of high aspect ratio features. Therefore, ozone gas has been used in some instances to overcome certain limitations of liquid-based processes because gases do not suffer from the same surface tension limitations. However, ozone- and plasma-based processes present their own set of limitations, including, inter alia, cost of operation, insufficient process controls, poor penetration into narrow high aspect ratio structures, undesired side reactions, and inefficient cleaning.

More recently, hydrogen peroxide has been explored as a replacement for ozone in certain applications. However, hydrogen peroxide has been of limited utility because highly concentrated hydrogen peroxide solutions present serious safety and handling concerns and obtaining high concentrations of hydrogen peroxide in the gas phase has not been possible using existing technology. Hydrogen peroxide is typically available as an aqueous solution. In addition, because hydrogen peroxide has a relatively low vapor pressure (boiling point is approximately 150° C.), available methods and devices for delivering hydrogen peroxide generally do not provide hydrogen peroxide containing gas streams with a sufficient concentration of hydrogen peroxide. For vapor pressure and vapor composition studies of various hydrogen peroxide solutions, see, e.g., Hydrogen Peroxide, Schumb, et al., Reinhold Publishing Corporation, 1955, New York, available at hdl.handle.net/2027/mdp.39015003708784. Moreover, studies show that delivery into vacuum leads to even lower concentrations of hydrogen peroxide (see, e.g., Hydrogen Peroxide, Schumb, pp. 228-229). The vapor composition of a 30% $H_2O_2$ aqueous solution delivered using a vacuum at 30 mm Hg is predicted to yield approximately half as much hydrogen peroxide as would be expected for the same solution delivered at atmospheric pressure.

Gas phase delivery of low volatility compounds presents a particularly unique set of problems. One approach is to provide a multi-component liquid source wherein the process chemical is mixed with a more volatile solvent, such as water or an organic solvent (e.g., isopropanol). However, when a multi-component solution is the liquid source to be delivered (e.g., hydrogen peroxide and water), Raoult's Law for multi-component solutions becomes relevant. According to Raoult's Law, for an idealized two-component solution, the vapor pressure of the solution is equal to the weighted sum of the vapor pressures for a pure solution of each component, where the weights are the mole fractions of each component:

$$P_{tot} = P_a x_a + P_b x_b$$

In the above equation, $P_{tot}$ is the total vapor pressure of the two-component solution, $P_a$ is the vapor pressure of a pure solution of component A, $x_a$ is the mole fraction of component A in the two-component solution, $P_b$ is the vapor pressure of a pure solution of component B, and $x_b$ is the mole fraction of component B in the two-component solution. Therefore, the relative mole fraction of each component is different in the liquid phase than it is in the vapor phase above the liquid. Specifically, the more volatile component (i.e., the component with the higher vapor pressure) has a higher relative mole fraction in the gas phase than it has in the liquid phase. In addition, because the gas phase of a typical gas delivery device, such as a bubbler, is continuously being swept away by a carrier gas, the composition of the two-component liquid solution, and hence the gaseous head space above the liquid, is dynamic.

Thus, according to Raoult's Law, if a vacuum is pulled on the head space of a multi-component liquid solution or if a traditional bubbler or vaporizer is used to deliver the solution in the gas phase, the more volatile component of the liquid solution will be preferentially removed from the solution as compared to the less volatile component. This limits the concentration of the less volatile component that can be delivered in the gas phase. For instance, if a carrier gas is bubbled through a 30% hydrogen peroxide/water solution, only about 295 ppm of hydrogen peroxide will be delivered, the remainder being all water vapor (about 20,000 ppm) and the carrier gas.

The differential delivery rate that results when a multi-component liquid solution is used as the source of process gases make repeatable process control challenging. It is difficult to write process recipes around continuously changing mixtures. In addition, controls for measuring a continuously changing ratio of the components of the liquid source are not readily available, and if available, they are costly and difficult to integrate into the process. In addition, certain solutions become hazardous if the relative ratio of the components of the liquid source changes. For example, hydrogen peroxide in water becomes explosive at concentrations over about 75%; and thus, delivering hydrogen peroxide by bubbling a dry gas through an aqueous hydrogen peroxide solution, or evacuating the head space above such solution, can take a safe solution (e.g., 30% w/w $H_2O_2/H_2O$) and convert it to a hazardous material that is over 75% hydrogen peroxide. Therefore, currently available delivery devices and methods are insufficient for consistently, precisely, and safely delivering controlled quantities of process gases in many micro-electronics applications and other critical processes.

Currently, no other proven technology exists for gas phase measurement of hydrogen peroxide. Ando et al. (U.S. Pat. No. 5,608,156) disclose using a semiconductor gas sensor as a means for measuring vapor phase $H_2O_2$ concentrations. However, the reaction time is tens of seconds and the relation between the sensor output and the concentration of $H_2O_2$ varies with pressure. Van Den Berg et al. (U.S. Pat. No. 5,600,142) disclose Fourier-transform infrared spectroscopy (FT-IR) based methods. However, FT-IR methods are large, very expensive and use mirrors that can decompose the $H_2O_2$ into water resulting in false low readings for hydrogen peroxide and false high readings for water vapor. As stated in Freyer et al. (U.S. Pat. No. 6,491,881) water spectra and organics can overlap with $H_2O_2$ spectra negatively. Further, ultraviolet-visible spectroscopy (UV-Vis) based sensors that were developed for ozone need to be heated and calibrated frequently when used with $H_2O_2$. As such, they cannot handle high concentrations and fail at high temperatures. In addition water signals may overlap with $H_2O_2$ and require an additional zeroing step to separate the $H_2O_2$ from the water vapor before making accurate readings. The heating can cause decomposition of the $H_2O_2$ before reaching the sensor. Hill et al. (U.S. Pat. No. 6,953,549) discusses measuring $H_2O_2$ vapor concentration by destroying the $H_2O_2$ and then measuring the moisture content. $H_2O_2$ vapor concentration for process development requires that humidity measurement be over determined. Further, in order to calculate mass flow rate, each of temperature, pressure, total gas flow rate, base line water vapor, and oxygen generated during destruction must be accurately known. In addition, destruction of the $H_2O_2$ requires the sensor be placed after the process where it is used. This can be inconvenient or not possible since other gases in the process recipe may not be compatible with the humidity sensor. Foller (Intl. Pub. No. WO1991/005998) describes a thermal decomposition sensor for measuring the concentration of ozone or chlorine oxide. Karlson (U.S. Pat. No. 5,167,927) describes a catalyst system for measuring the temperature of catalytic decomposition of ozone or hydrogen peroxide. Nather et al. (Intl. Pub. No. WO2006/117328) describes a thermal decomposition detector for measuring the concentration of $H_2O_2$ vapor.

However, each of these references rely upon exothermic energy released during the decomposition of the target molecule to generate an electric signal to indicate the presence of a combustible gas. However, none of these sensors is capable of being used in semiconductor process applications where the output signal must cover a large range of process conditions and output an electrical signal that is proportional to the change in concentration. Description of tracking in a dilute gas stream under vacuum was also not discussed; neither was determining that process control for dilute $H_2O_2$ vapor could be controlled by measuring the $H_2O_2$ concentration and then using the generated electric signal to increase or decrease the temperature of the $H_2O_2$ vapor for stabilizing delivery of the $H_2O_2$ vapor to a process. Therefore, a need exists for a system, method and/or device for in-line measurement of catalytically reactive gases, such as hydrogen peroxide, provided in a mixed gas stream in order to control mass flow rate of the catalytically reactive gas delivered to a process, such as microelectronics manufacturing.

SUMMARY OF THE INVENTION

The present invention is based on the observation that determining thermal rise due to decomposition of a catalytically reactive gas in a mixed gas stream correlates with concentration of the catalytically reactive gas. Accordingly, in one aspect, the invention provides a mass flow control system for controlling mass flow rate of a catalytically reactive gas within a mixed gas stream. The mass flow control system includes a mixed gas source providing a mixed gas stream, the mixed gas stream comprising a catalytically reactive gas generated from a gas or liquid source and a carrier gas, a first sensor comprising a first probe configured to measure a first temperature of the mixed gas stream, a decomposition chamber configured to accept a portion of the mixed gas stream, wherein the decomposition chamber comprises a catalyst configured to decompose with the catalytically reactive gas, a second sensor comprising a second probe disposed within the decomposition chamber and configured to measure a second temperature of the mixed gas stream following reaction between the catalyst and the catalytically reactive gas, a controller in electrical communication with the first and second sensors, wherein the controller is configured to determine the mass flow of the catalytically reactive gas by determining a change in temperature prior to and following contact of the mixed gas stream with the catalyst, and an effector in electrical communication with the controller, wherein the effector is configured to change the mass flow rate of the catalytically reactive gas by adjusting temperature of the liquid source, head space pressure of the liquid source or the carrier gas mass flow rate, or any combination thereof.

In various embodiments, the change in temperature is approximately proportional with the change in catalytically reactive gas mass flow rate. In various embodiments, the change in temperature is relatively independent of the pressure or flow rate of the mixed gas stream. In various embodiments, the catalytically reactive gas may be generated from a liquid source. In various embodiments, the mass flow control system may also include a first heater configured to heat the catalyst to a temperature above the dew point of the catalytically reactive gas and a third sensor comprising a third probe disposed at the decomposition chamber and configured to measure a third temperature of the heated catalyst. The first heater may further be in electrical communication with the controller.

The catalyst may be chosen to be appropriate for reaction with the catalytically reactive gas. In various embodiments, the catalyst is selected from the group consisting of silver, platinum, palladium, copper, nickel, other precious metals, manganese oxide, manganese dioxide, copper oxide, and any combination thereof. In various embodiments, CARULITE® 200, CARULITE® 300, and CARULITE® 400. The catalyst may be coated on an aluminum temperature sensor. The catalytically reactive gas may be hydrogen peroxide gas or hydrazine. Thus, in various embodiments, the mixed gas stream may include hydrogen peroxide gas and a carrier gas such as nitrogen, hydrogen, argon, helium, steam, clean dry air, oxygen, $NH_3$, carbon dioxide, and optionally, water vapor. In various embodiments, the liquid source is selected from the group consisting of anhydrous hydrogen peroxide and anhydrous hydrazine.

In various embodiments, the mass flow rate delivered by the system is between about 1 milligram per minute and 10 gram per minute. In various embodiments, the mixed gas stream is provided at a pressure of about 10 Torr to 2 barg. In various embodiments, the concentration of catalytically reactive gas is about 100 parts per million (ppm) to about 100,000 ppm (10%), such as about 500 ppm to about 25,000 ppm. In various embodiments, the mixed gas stream is provided at about 0.076 Torr to 800 Torr. In embodiments where the system is operating under a vacuum, the pressure of the mixed gas stream provided to the system is about 10.0 to 100.0 Torr. In various embodiments, the mixed gas stream is provided at about 15° C. to about 150° C., such as about 20° C. to about 80° C. or about 15° C. to about 80° C. The effector may be a pressure regulating valve disposed upstream of the liquid source, a pressure regulating valve disposed downstream of the liquid source, a heater configured to regulate the temperature of the liquid source, or a chiller configured to regulate the temperature of the liquid source.

In another aspect, the invention provides a mass flow control system for controlling mass flow rate of a catalytically reactive gas within a mixed gas stream. The mass flow control system includes a mixed gas source providing a mixed gas stream, the mixed gas stream comprising a catalytically reactive gas such as ozone gas generated from an ozone generator and a carrier gas, a first sensor comprising a first probe configured to measure a first temperature of a mixed gas stream, a decomposition chamber configured to accept a portion of the mixed gas stream, wherein the decomposition chamber comprises a catalyst configured to decompose with the catalytically reactive gas, a second sensor comprising a second probe disposed within the decomposition chamber and configured to measure a second temperature of the mixed gas stream following reaction between the catalyst and the catalytically reactive gas, a controller in electrical communication with the first and second sensors, wherein the controller is configured to determine the mass flow of the catalytically reactive gas by determining a change in temperature prior to and following contact of the mixed gas stream with the catalyst, and an effector in electrical communication with the controller, wherein the effector is configured to adjust temperature, power, pressure or mass flow rate of the mixed gas source to change the mass flow rate of the catalytically reactive gas.

The catalyst may be chosen to be appropriate for reaction with the catalytically reactive gas. In various embodiments, the catalyst is selected from the group consisting of silver, platinum, palladium, copper, nickel, other precious metals, manganese oxide, manganese dioxide, copper oxide, and any combination thereof. In various embodiments, CARULITE® 200, CARULITE® 300, and CARULITE® 400. The catalyst may be coated on an aluminum temperature sensor. Thus, in various embodiments, the mixed gas stream may include oxygen radicals and/or ozone from an ozone generator and a carrier gas such as nitrogen, hydrogen, argon, helium, steam, clean dry air, oxygen, $NH_3$, carbon dioxide, where the carrier gas is chosen to be non-reactive with the chosen catalyst. In various embodiments, the concentration of the catalytically reactive gas is about 100 parts per million (ppm) to about 95% (950,000 ppm), such as about 1000 ppm to about 900,000 ppm. In various embodiments, the mixed gas stream is provided at about 0.10 Torr to 800 Torr. In various embodiments, the mixed gas stream is provided at about 15° C. to about 350° C., such as about 20° C. to about 150° C. The effector may be a power supply configured to deliver power to the ozone generator.

In various embodiments, the change in temperature is approximately proportional with the change in catalytically reactive gas mass flow rate. In various embodiments, the change in temperature is relatively independent of the pressure or flow rate of the mixed gas stream. In various embodiments, the mass flow control system may also include a first heater configured to heat the catalyst to a temperature above the dew point of the catalytically reactive gas and a third sensor comprising a third probe disposed at the decomposition chamber and configured to measure a third temperature of the heated catalyst. The first heater may further be in electrical communication with the controller.

In various embodiments, the above-disclosed elements of the mass flow control system may be disposed in a housing. In various embodiments, the housing includes an inlet, a first tube configured to provide fluid communication with between the inlet and the decomposition chamber, an outlet, and a second tube configured to provide fluid communication between the decomposition chamber and the outlet. The first sensor may be disposed within the first tube and the second sensor may be disposed in the decomposition chamber or the second tube. In various embodiments, the mass flow control system may also include a heater disposed in contact with the decomposition chamber and configured to heat the catalyst to a temperature above the dew point of the catalytically reactive gas, and a third sensor comprising a third probe disposed at within the decomposition chamber and configured to measure a third temperature of the catalyst. In various embodiments, the housing is provided in a vacuum and the mixed gas stream is provided at least about 0.3 Torr to 800 Torr.

In another aspect, the invention provides a method of controlling mass flow of a dilute catalytically reactive gas in a mixed gas stream. The method includes providing a mixed gas stream from a mixed gas source, the mixed gas stream comprising a dilute catalytically reactive gas generated from a liquid source, and a carrier gas, determining a first temperature of the mixed gas stream, exposing at least a portion of the mixed gas stream to a catalyst configured to react with the catalytically reactive gas, determining a second temperature of the mixed gas stream following reaction between the catalyst and the catalytically reactive gas, determining mass flow of the catalytically reactive gas by determining a change in temperature following contact of the mixed gas stream with the catalyst, wherein the change in temperature is relatively independent of the pressure or flow rate of the mixed gas stream, and adjusting one or more of temperature of the liquid source, pressure of a headspace of the liquid source, and carrier gas flow rate to achieve a desired mass flow rate of the dilute catalytically reactive gas. In various embodiments any of the steps may be repeated to achieve a desired mass flow rate of the dilute catalytically reactive gas. In various embodiments, the mixed gas stream is provided at about 0.076 Torr to about 800 Torr, such as at least about 10.0 Torr to about 100.0 Torr. In various embodiments, the mixed gas stream is provided at about 15° C. to about 150° C., such as about 20° C. to about 80° C. In various embodiments, the method also includes heating the catalyst to a temperature above the dew point of the catalytically reactive gas prior to exposing to the mixed gas stream.

In various embodiments, the step of adjusting is accomplished using an effector. The effector may be a pressure regulating valve disposed upstream of the liquid source, a pressure regulating valve disposed downstream of the liquid source, a heater configured to regulate the temperature of the liquid source, or a chiller configured to regulate the temperature of the liquid source. In various embodiments, the total amount of the catalytically reactive gas in the mixed gas stream is provided at about 100 ppm to about 100,000 ppm, such as about 500 ppm to 25,000 ppm.

The catalyst would be chosen to be appropriate for reaction with the catalytically reactive gas. In various embodiments, the catalyst is selected from the group consisting of silver, platinum, palladium, copper, nickel, other precious metals, manganese oxide, manganese dioxide, copper oxide, and any combination thereof. In various embodiments, CARULITE® 200, CARULITE® 300, and CARULITE® 400. The combustible gas may be hydrogen peroxide gas, ozone, or hydrazine ($H_2N_4$). Thus, in various embodiments, the mixed gas stream may include hydrogen peroxide gas and a carrier gas such as nitrogen, hydrogen, argon, helium, steam, clean dry air, oxygen, $NH_3$, and carbon dioxide, and optionally, water vapor. In various embodiments, the method includes heating the mixed gas stream prior to exposing to the catalyst. In various embodiments, the invention may be used in conjunction with a control valve such that the amount of catalytically reactive gas can be regulated by limiting the flow rate based on the signal from the sensor. Similarly, control of the catalytically reactive gas may be exerted by adding or reducing heat to the liquid or adding or reducing power to the ozone source to raise or lower the flow rate.

In yet another aspect, the invention provides a thermal decomposition sensor. The thermal decomposition sensor includes a housing having an inlet and an outlet, a decomposition chamber disposed within the housing and containing a catalyst configured to decompose with a catalytically reactive gas of a mixed gas stream, wherein the decomposition chamber is configured to accept a portion of the mixed gas stream provided to the inlet of the housing and wherein the mixed gas stream comprises the catalytically reactive gas and a carrier gas, a first tube disposed within the housing and providing fluid communication between the inlet and the decomposition chamber, a second tube disposed within the housing and providing fluid communication between the decomposition chamber and the outlet, a first sensor having an integrated first probe disposed within the first tube and configured to measure a first temperature of the mixed gas stream provided to the inlet, and a second sensor having an integrated second probe disposed within the second tube and configured to measure a second temperature of the carrier gas following reaction between the catalyst and the catalytically reactive gas. In various embodiments, the thermal decomposition sensor also includes a heater disposed within the housing and configured to heat the catalyst to a temperature above the dew point of the catalytically reactive gas, and a third sensor having a third integrated probe disposed at the heater and configured to measure a third temperature of the catalyst.

DETAILED DESCRIPTION OF THE INVENTION

Figure 1A:
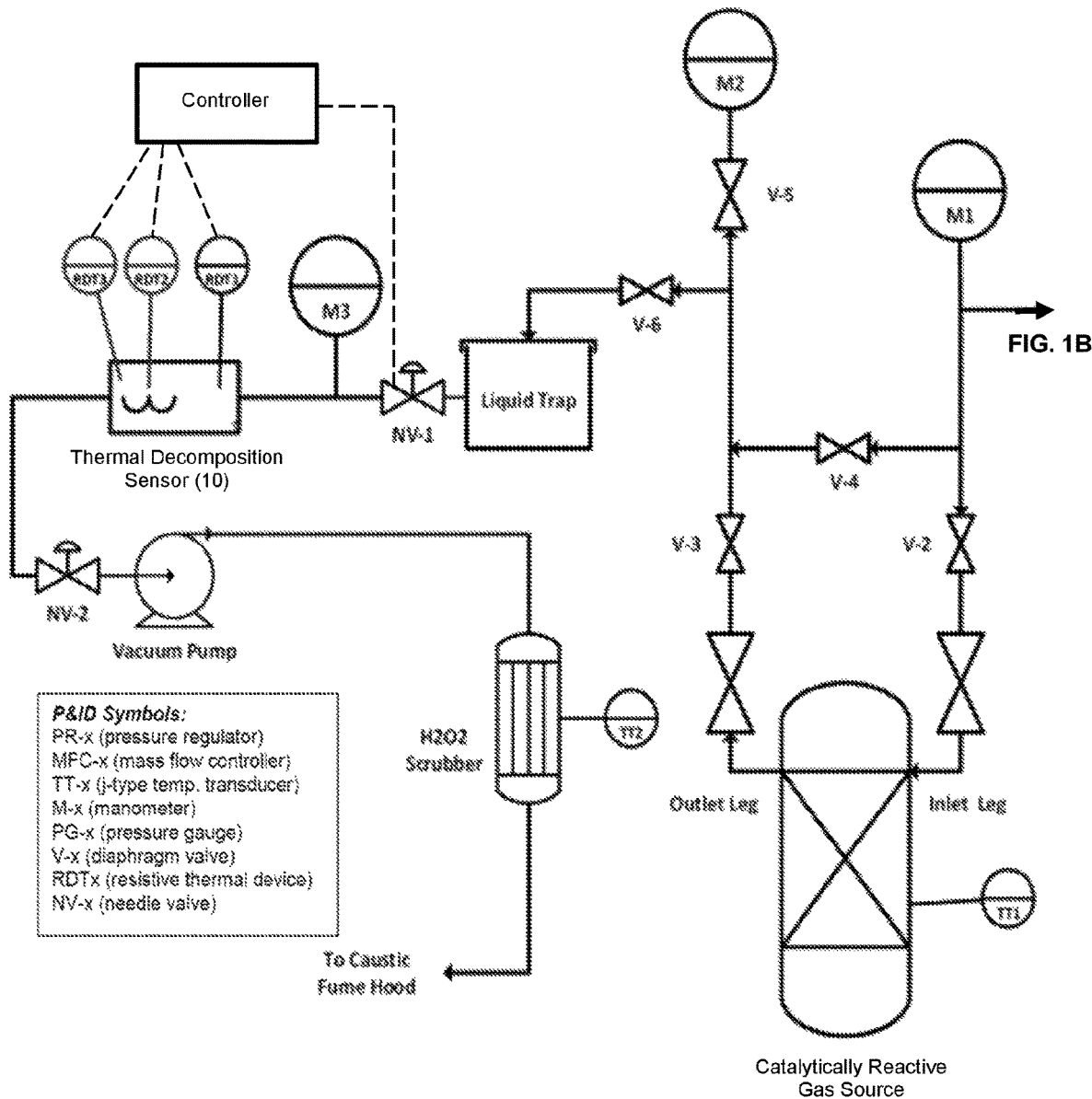
FIGS. 1A and 1B are pictorial diagrams showing an exemplary experimental P&ID.

The present invention is based on the observation that determining thermal rise due to decomposition of a catalytically reactive gas in a mixed gas stream correlates with concentration of the catalytically reactive gas. Since the catalytically reactive gas easily decomposes at low temperatures on different active metal surfaces (catalysts), the change in temperature following reaction with the catalyst provides the ability to monitor the catalytically reactive gas in the mixed gas stream independently from any carrier gases. As such, the present invention provides methods, systems, and apparatus for controlling and/or measuring mass flow rate of a catalytically reactive gas, such as hydrogen peroxide gas, when used in any passivation or oxidation process for semiconductor, microelectronics, displays, and LEDs, as well as for sterilization including food service, medical, hospital, and transportation.

As such, the present invention provides a thermal decomposition sensor configured to (i) enable measurement of a dilute combustible gas in a carrier gas; (ii) provide a linear output signal with a linear change in the mass flow of the combustible gas while holding the carrier gas flow relatively constant; (iii) enable measurement of a dilute combustible gas in a carrier gas under vacuum pressures to provide continuous monitoring of a critical process; (iv) enable precise control of delivery of a dilute combustible gas in a carrier gas by comparing the actual amount of combustible gas in the carrier gas with a desired setpoint, and then allowing for adjustment of the amount of combustible gas by various means to increase or decrease the amount of combustible gas so that the measured amount of combustible gas is within an acceptable range of the setpoint; (v) enable precise control and repeatability of the delivered combustible gas by allowing the catalyst to be heated to a fixed temperature above the condensation temperature of the dilute combustible gas.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

"Molar ratio," as used herein, is commonly understood to mean that, for a mixed gas stream, the molar ratio for any specific gas component would be the molar flow rate for the individual gas component divided by the total molar flow rate for the entire mixed gas stream. The ratio is commonly used as a percentage where the ratio is then multiplied by 100.

As used herein, a "carrier gas" is a gas that is used to enhance mass transportation of a target gas mass transfer rate that does not generally react with a catalyst for the target gas. Thus, a carrier gas is typically an inert gas such as, but not limited to, nitrogen, hydrogen, argon, helium, steam, clean dry air, oxygen, $NH_3$, and carbon dioxide, and optionally, water vapor.

As used herein, a "mass flow meter" or "MFM" is a device that measures mass flow rate of a fluid traveling through a tube, pipe, or enclosed channel. The "mass flow rate" is the mass of the fluid traveling past a fixed point per unit time. Thus, volumetric flow rate of fluids is the mass flow rate divided by the fluid density. For gases, the ideal gas law is used to determine the volumetric flow rate, which is measured in standard liters per minute (22.4 L/mol).

As used herein, a "mass flow controller" or "MFC" is a device used to measure and control the flow of liquids and gases. A mass flow controller is designed and calibrated to control a specific type of liquid or gas at a particular range of flow rates. The MFC can be given a setpoint from 0 to 100% of its full scale range but is typically operated in the 10 to 90% of full scale where the best accuracy is achieved. The device will then control the rate of flow to the given setpoint. As such, a major difference between MFC and MFM is that an MFC includes an active component (effector) to increase or decrease the mass flow rate. Exemplary active components (effectors) include, but are not limited to, a fluid valve, pressure regulating valve, a downstream thermal input (heater) configured to regulated temperature of the liquid source, a chiller configured to regulate the temperature of the liquid source, a power supply configured to deliver power to the ozone generator, or any combination thereof.

As used herein, "resistance temperature detector" or "RTD" refers to a temperature sensor that contains a resistor that changes resistance value as its temperature changes. Typically, such temperature sensors include an integrated or external probe and the combination of resistance tolerance and temperature coefficient define the resistance vs. temperature characteristics for the RTD sensor. For example, the larger the element tolerance, the more the sensor will deviate from a generalized curve, and the more variation there will be from sensor to sensor (interchangeability).

As used herein, "thermocouple" or "TC" refers to an electrical device consisting of two dissimilar conductors forming electrical junctions at differing temperatures. A thermocouple produces a temperature-dependent voltage as a result of the thermoelectric effect, and this voltage can be interpreted to measure temperature.

As used herein, the terms "condensation temperature" and "dew point" of a catalytically reactive gas are used synonymously to refer to the temperature (at a given pressure) at which the catalytically reactive gas will begin to condense out of the gaseous phase.

Customer applications for hydrogen peroxide vapor require highly stable and repeatable chemical delivery in order to achieve good process control. For example, atomic layer deposition requires the ability to measure in vacuum and atmospheric pressure the concentration of precursor chemistry delivered to the wafer. An anhydrous hydrogen peroxide and organic solvent formulation, known as BRUTE® Peroxide (RASIRC, Inc., San Diego, Calif.) is continuously slowly decomposing into water and oxygen. Further, during usage of the formulation, $H_2O_2$ is consumed so the vapor pressure of hydrogen peroxide gas is constantly decreasing and therefore, the molar ratio to the carrier gas is also constantly decreasing. Thus, the system and device disclosed herein provides the ability for in-line measurement and mass flow control of a catalytically reactive gas, such as hydrogen peroxide, in order to control the output of the catalytically reactive gas delivered to a process. As demonstrated herein, the system and device stabilize output of hydrogen peroxide gas delivered from an ampoule of BRUTE® Peroxide. In various embodiments, the stabilized delivery is accomplished by measuring the output of hydrogen peroxide gas and providing for closed loop adjustment of the ampoule temperature.

The design elements of a thermal MFC commonly used to measure compressed gas are well known to those in the art. Manufacturers such as Horiba, STEC, and Brooks produce MFC and MFM with the ability to measure at better than 1% accuracy for a gas flow. However, when two or more gases are mixed together in an unknown ratio, it is not possible to know the new specific heat of the combined mixed gas stream. As such, a mixture of, for example, hydrogen peroxide gas, water vapor, and carrier gas would provide a single output for any flow condition, but the amount of hydrogen peroxide gas would still be unknown. In addition, the catalytically reactive gas is added as a dopant for a process. Thus, the amount added may be less than 10%, may be less than 1%, may be less than 0.1%, and may be less than 0.01% as commonly referred to in ppm or parts per million. The amount added is frequently between 0.1% and 2.5%. This small amount of material, when added, will not generate a measurable signal in a standard type of thermal MFC. As such, a standard MFC or MFM cannot be used in this application because the hydrogen peroxide gas molecules are delivered with a carrier gas and include water vapor. Due to the mix of gases, mass flow controllers cannot selectively measure the hydrogen peroxide gas content. Other analytical methods such as UV-Vis or FT-IR are either ineffective in a vacuum or are too clumsy, large, and/or expensive for integration into OEM Semiconductor atomic layer deposition (ALD) equipment.

The integration of a hydrogen peroxide vapor concentration sensor will allow for closed loop control of output of hydrogen peroxide vapor from PPM (parts per million ($10^6$) by volume) to percentage (%). This will be enabled by raising or lowering the temperature in the hydrogen peroxide vaporizer or through regulating the pressure above the headspace of the liquid source. This will eliminate the need to develop an algorithm that can take into account flow rate, hydrogen peroxide concentration, and hydrogen peroxide bath temperature. It will also eliminate the output sensitivity to thermal droop as the vaporizer temperature stabilizes. As the membrane is exposed to contaminants such as stabilizers, the throughput with temperature will drop. A hydrogen peroxide vapor sensor will mitigate this drift.

Accordingly, the present disclosure provides a thermal decomposition sensor based on the heat of decomposition of a catalytically reactive gas (e.g., hydrogen peroxide gas, hydrazine ($H_2N_4$), or ozone) to enable measuring the mass flow of the catalytically reactive gas at atmospheric pressure and sub-atmospheric pressure. In various embodiments, the catalytically reactive gas may be generated from a liquid source or a gas source. In certain embodiments, the catalytically reactive gas is ozone that may be generated using an ozone generator.

One key characteristic of hydrogen peroxide gas is that it easily decomposes at low temperatures on different active metal surfaces. The decomposition of hydrogen peroxide gas is highly exothermic. By using proven thermal sensor technology and adding a catalyst to decompose the gas, the system and device of the present invention is able to monitor the hydrogen peroxide gas in a mixed gas stream relatively independent of the water vapor and the carrier gas. The resulting mass flow control system may therefore find application in controlling mass flow rate of a catalytically reactive gas within a mixed gas stream.

In one embodiment, the system includes a mixed gas source 50 providing a mixed gas stream G, the mixed gas stream including a catalytically reactive gas and a carrier gas. In various embodiments, the mixed gas stream may be generated from a liquid or gas source. The system also includes a first sensor comprising a probe configured to measure a first temperature of a mixed gas stream containing the catalytically reactive gas, a decomposition chamber configured to accept a portion of the mixed gas stream, wherein the decomposition chamber contains a catalyst configured to react with the catalytically reactive gas. The system also includes a second sensor comprising a probe disposed within the decomposition chamber and configured to measure a second temperature of the mixed gas stream following reaction between the catalyst and the catalytically reactive gas. In various embodiments, the system further includes a controller in electrical communication with the first and second sensors, wherein the controller is configured to determine the mass flow of the catalytically reactive gas by determining a change in temperature prior to and following contact of the mixed gas stream with the catalyst. In various embodiments, the system also includes an effector in electrical communication with the controller, wherein the effector is configured to adjust the mass flow rate of the catalytically reactive gas by adjustment of any one or more of: temperature of the liquid source; head space pressure of the liquid source; or power, pressure, or gas flow to the ozone source.

Exemplary catalysts useful in the device include, but are not limited to, silver, platinum, palladium, copper, nickel, other precious metals, manganese oxide, manganese dioxide, copper oxide, and any combination thereof. In various embodiments, the catalyst is CARULITE® 200, CARULITE® 300, or CARULITE® 400. In various embodiments, the catalyst is coated on a stainless steel or an aluminum temperature sensor.

In another aspect, the invention provides a method for controlling mass flow of a dilute catalytically reactive gas in a mixed gas stream. The method includes providing a mixed gas stream from a mixed gas source, where the mixed gas stream contains the dilute catalytically reactive gas and a carrier gas, followed by determining a first temperature of the mixed gas stream. Thereafter, the method includes exposing at least a portion of the mixed gas stream to a catalyst configured to react with the catalytically reactive gas, and determining a second temperature of the mixed gas stream following reaction between the catalyst and the catalytically reactive gas. The method also includes determining mass flow of the catalytically reactive gas by determining a change in following contact of the mixed gas stream with the catalyst, wherein the change in temperature is relatively independent of the pressure or flow rate of the mixed gas stream. Finally, the method includes adjusting one or more of temperature of the liquid source, pressure of a headspace of the liquid source, and carrier gas flow rate to achieve a desired mass flow rate of the dilute catalytically reactive gas. In various embodiments, the method includes heating the catalyst to a temperature above the dew point of the catalytically reactive gas prior to exposing to the mixed gas stream. In various embodiments, the method may also include heating the mixed gas stream prior to exposing to the heated catalyst. In various embodiments any of the steps may be repeated to achieve a desired mass flow rate of the dilute catalytically reactive gas.

In yet another aspect, the invention provides a thermal decomposition sensor 10, which includes an inlet 12, a first tube 14, a second tube 16, and an outlet 18, all of which are disposed in a housing 20. Disposed within the first tube 14 is a first sensor 24 having an integrated first probe 36 configured to measure the temperature of the incoming mixed gas stream G. Provided in fluid communication with the first tube 14 and the second tube 16 is a decomposition chamber 26 configured to accept at least a portion of the incoming mixed gas stream G. Disposed within the decomposition chamber 26 is a catalyst 28 configured to decompose with the catalytically reactive gas within the mixed gas stream G. In various embodiments, the decomposition chamber 26 may also include a heater 30 configured to heat the catalyst to a temperature above the dew point of the catalytically reactive gas and/or configured to heat the incoming mixed gas stream G prior to contact with the catalyst. Disposed within the second tube 16 is a second sensor 32 having an integrated second probe 36 configured to measure the temperature of the carrier gas following reaction between the catalyst 28 and the catalytically reactive gas. In various embodiments, a third sensor 34 with integrated probe 36 may be disposed at the heater 30 or within the decomposition chamber 26 when the second sensor 32 is disposed within the second tube 16, and configured to measure the temperature of the catalyst 28 and/or the decomposition chamber 26.

While the present disclosure demonstrates use of the system in conjunction with delivery of hydrogen peroxide in process systems, it is envisioned that the system may be used for other gases that decompose or otherwise react with a catalyst, such as, for example hydrazine or ozone.

The following examples are intended to illustrate but not limit the invention.

EXAMPLE 1

Figure 1B:
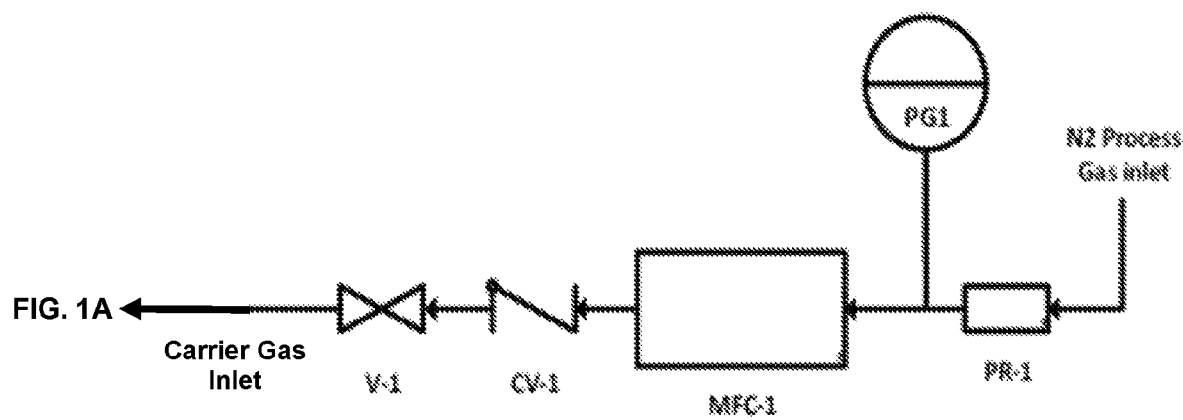

FIGS. 1A and 1B show an exemplary experimental setup for testing thermal response of $H_2O_2$ vapor decomposition under vacuum using catalytic materials fixed to resistive thermal devices. It should be understood that the system shown in FIGS. 1A and 1B may be used for providing controlled delivery of any of $H_2O_2$, hydrazine ($H_2N_4$) or ozone with minor modifications thereto. For this experiment, 300 mg of Carulite-300 was packed around RTD 2 and held captive by two 80 mesh stainless steel screens on each side of RTD 2. The diameter of the packed bed was 0.35" and the total packed bed length with screens was ~0.31". RTD 1 measured the inlet carrier gas temperature and RTD 3 measured the temperature of the carrier gas after decomposition in the packed bed. In this test set up, RTD 3 had a ⅜" gap between it and the packed bed such that thermal conduction is minimal.

Figure 2:
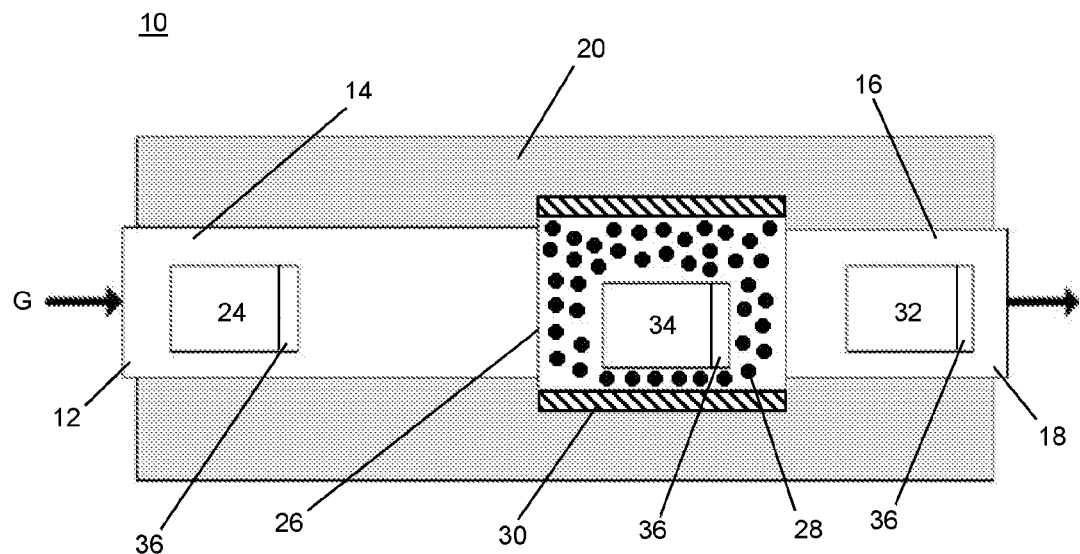
FIG. 2 is a pictorial diagram showing a cross-sectional view of an exemplary mass flow control sensor.

FIG. 2 shows an exemplary layout of the thermal decomposition sensor. As shown, the thermal decomposition sensor 10 includes an inlet 12, a first tube 14, a second tube 16, and an outlet 18, all of which are disposed in a housing 20. Disposed within the first tube 14 is a first sensor (resistance temperature detector; RTD 1) 24 having an integrated first probe 36 configured to measure the temperature of the incoming mixed gas stream G. Provided in fluid communication with the first tube 14 and the second tube 16 is a decomposition chamber 26 configured to accept at least a portion of the incoming mixed gas stream G. Disposed within the decomposition chamber 26 is a catalyst 28 configured to decompose with the catalytically reactive gas within the mixed gas stream G. In various embodiments, the decomposition chamber 26 may also include a heater 30 configured to heat the catalyst to a temperature above the dew point of the catalytically reactive gas and/or configured to heat the incoming mixed gas stream G prior to contact with the catalyst. Disposed within the second tube 16 is a second sensor (resistance temperature detector; RTD3) 32 having an integrated second probe 36 configured to measure the temperature of the carrier gas following reaction between the catalyst 28 and the catalytically reactive gas. In various embodiments, a third sensor (resistance temperature detector; RTD2) 34 with integrated probe 36 may be disposed at the heater 30 or within the decomposition chamber 26 when the second sensor 32 is disposed within the second tube 16, and configured to measure the temperature of the catalyst 28 and/or the decomposition chamber 26.

The thermal decomposition sensor (10) was installed downstream of a 1 L liquid trap. Pressure Regulator-1 (PR-1) was set to 8 psig, and the base pressure of M2 was set to 12 Torr±2 Torr. The test was repeated by setting the vaporizer head space pressure to 25, 50, and 75 Torr by adjusting NV-1 thereby delivering lower peroxide mass flowrates to the sensor and allowing for the formation of a calibration curve.

Figure 3:
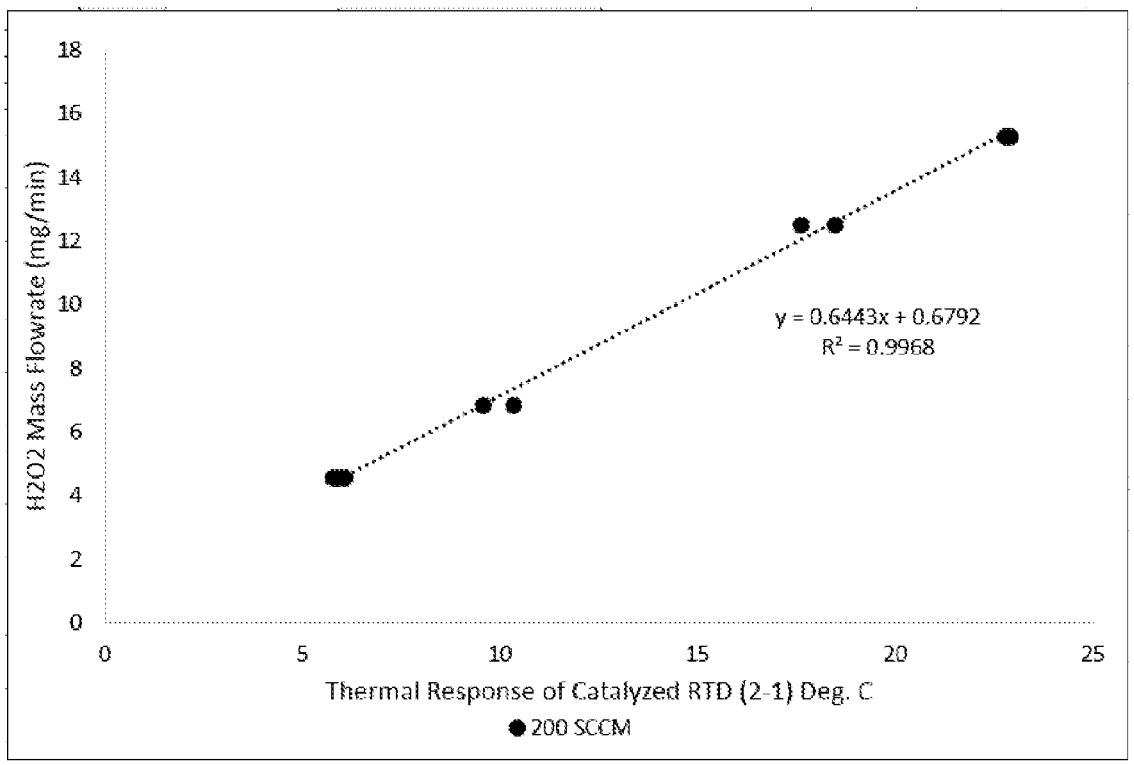
FIG. 3 is a graphical diagram showing thermal response of catalyzed resistive thermal device vs change in peroxide mass flow rate with the carrier gas flow rate held constant.
Figure 4:
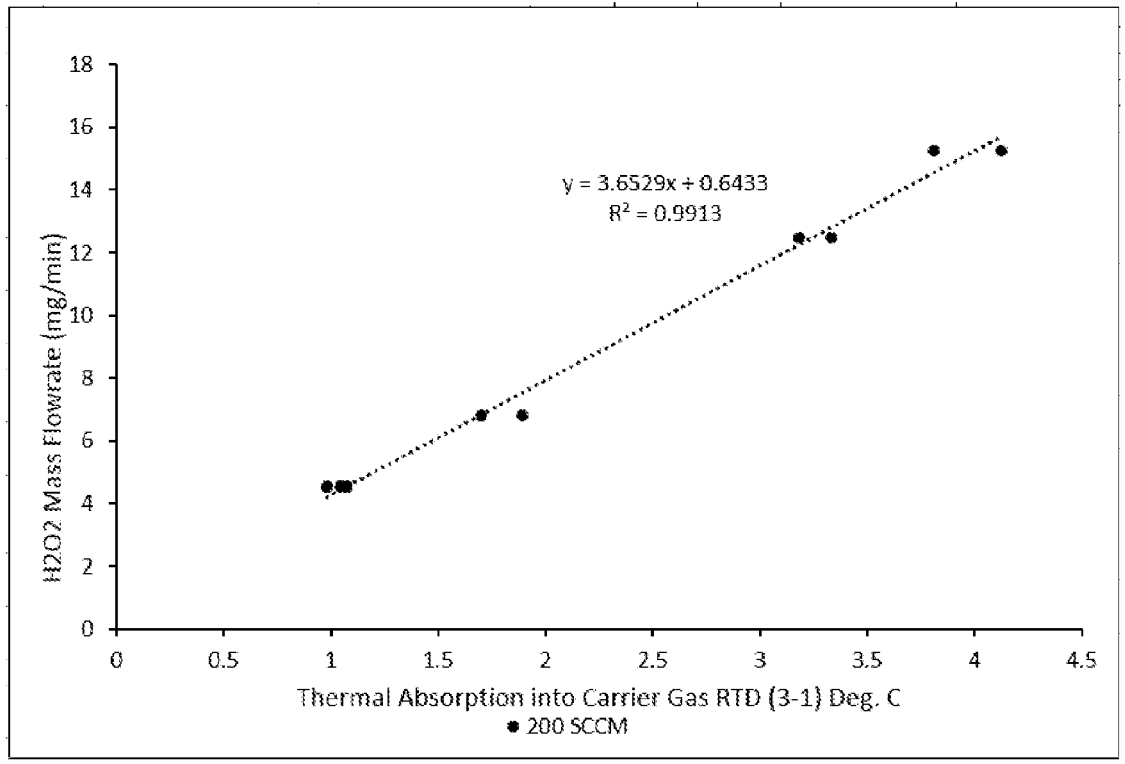
FIG. 4 is a graphical diagram showing thermal absorption of carrier gas downstream of the catalyst vs change in peroxide mass flow rate with the carrier gas flow rate held constant.

Four series of tests were completed on the Carulite-300 packed bed sensor under 200 sccm of nitrogen carrier gas flow. The headspace pressure was changed during each series from 75, 50, 25, to 12 Torr to vary the peroxide mass flowrate in the carrier gas stream while keeping the carrier gas flowrate constant. The resulting peroxide mass flowrates were 4.56, 6.83, 12.5, and 15.3 g/min, respectively. Table 1 summarizes the thermal response of the catalyzed packed bed (RTD2) and the thermal response of heat absorption into the carrier gas (RTD3). FIGS. 3 and 4 plot the results in Table 1 and fit linear correlations valid for 200 sccm and 9 Torr sensor pressure.

A 60 minute purge with dry nitrogen at the same carrier gas flowrate is ran before each 60 minute peroxide vapor exposure. The average mass flowrate delivered is calculated by the mass difference (before–after) and divided by the total H$_2$O$_2$ run time. For example, the total mass vaporized in the "4.56 mg/min test" was 0.82 g and this occurred over 180 minutes—three 60 minute pulses—when flowing 200 sccm through the vaporizer (i.e., 820 mg/180 min).

TABLE 1

Summary Table, Thermal Response of Sensor with 0.3 g Carulite-300 Packed Bed @ 200 sccm

| RTD (2-1) ° C. | RTD (3-1) ° C. | Average H$_2$O$_2$ Mass Flowrate by Scale (mg/min) |
|---|---|---|
| 5.9 | 1.04 | 4.56 |
| 5.75 | 1.07 | 4.56 |
| 6.04 | 0.98 | 4.56 |
| 9.57 | 1.7 | 6.83 |
| 10.33 | 1.89 | 6.83 |
| 18.45 | 3.18 | 12.5 |
| 17.58 | 3.33 | 12.5 |
| 22.75 | 3.81 | 15.3 |
| 22.88 | 4.12 | 15.3 |

The thermal responses of both the catalyzed packed bed RTD (2-1) and the heat absorption into the carrier gas RTD (3-1) were found to be linear; the R2 values for both curves were >0.99. At 9 Torr sensor pressure and 200 sccm of carrier gas flow, heat transfer into the carrier gas was found to be low. Under these conditions, the temperature increase in the catalyst bed was about 6 times greater than the temperature increase of the carrier gas.

Effects of Carrier Gas Flowrate:

The next series of tests vary the carrier gas flowrate through the sensor from 200, 350, to 500 sccm. The same procedure as described above was used. The purpose of these tests is to demonstrate how changing the carrier gas flowrate affects the equilibrium temperatures of RTD2 and RTD3. At each carrier gas flowrate, the BRUTE peroxide headspace pressure was adjusted using NV-1 to vary the H$_2$O$_2$ mass flowrates. The thermal responses for each carrier gas flowrate were grouped into individual series and compared (FIGS. 5 and 6).

Figure 5:
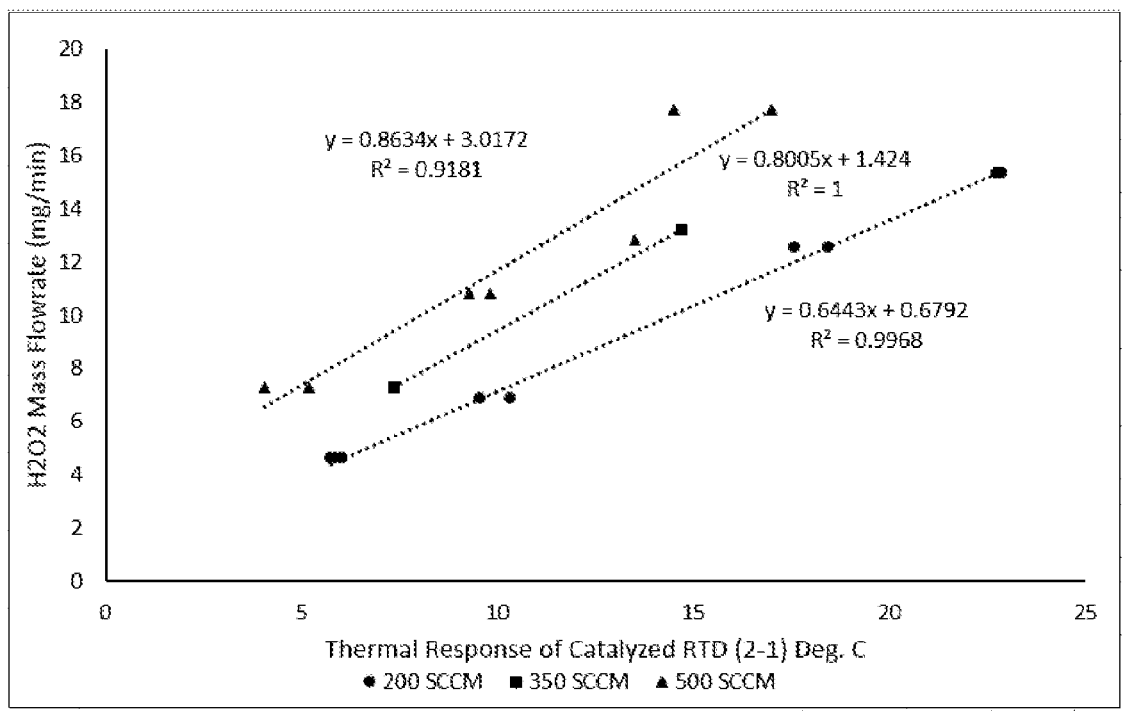
FIG. 5 is a graphical diagram showing thermal response of catalyzed resistive thermal device vs change in peroxide mass flow rate at different carrier gas flow rates.
Figure 6:
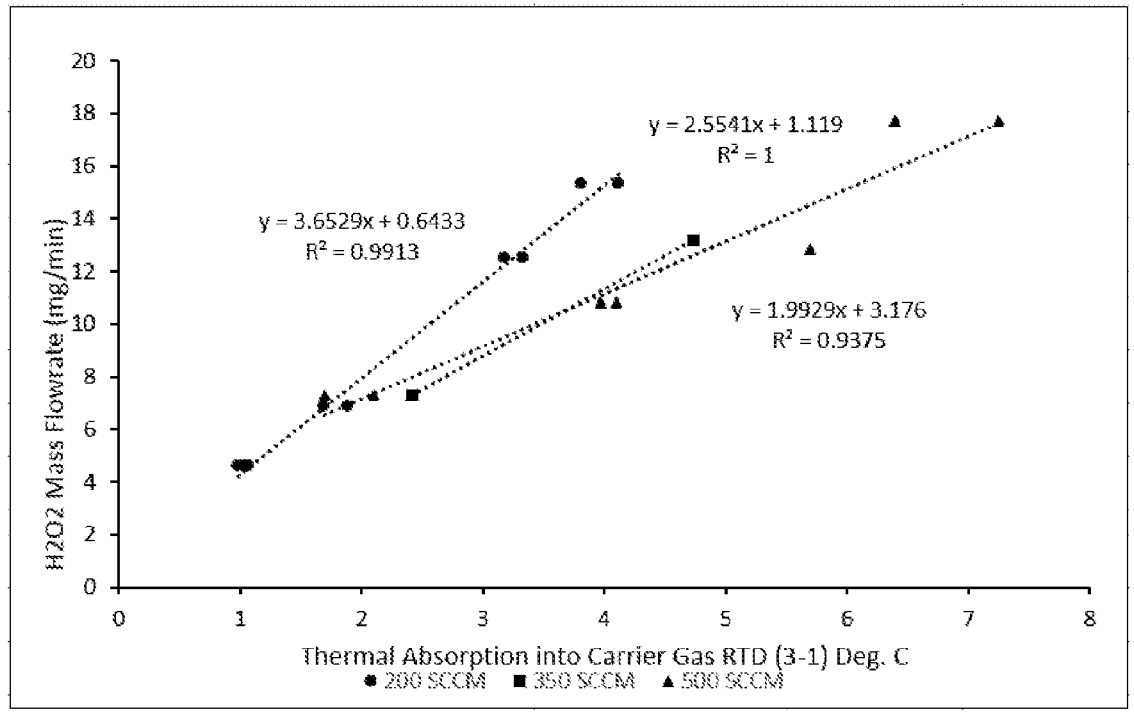
FIG. 6 is a graphical diagram showing thermal absorption of carrier gas vs change in peroxide mass flow rate downstream of the catalyst at different carrier gas flow rates.

As seen in FIG. 5, the equilibrium temperature of RTD (2-1) decreases as carrier gas flowrate increases for the same H$_2$O$_2$ mass flowrate (i.e., the linear trend gets shifted to the left with increasing carrier gas flowrate). On the contrary, the equilibrium temperature of RTD (3-1) increases as the carrier gas flowrate increases for the same H$_2$O$_2$ mass flowrate (i.e., the linear trend gets shifted to the right with increasing carrier gas flowrate (FIG. 6)).

Without being bound by theory, the equilibrium thermal ratio is defined below:

Equilibrium Thermal ratio=(2-1)/(3-1)

Figure 7:
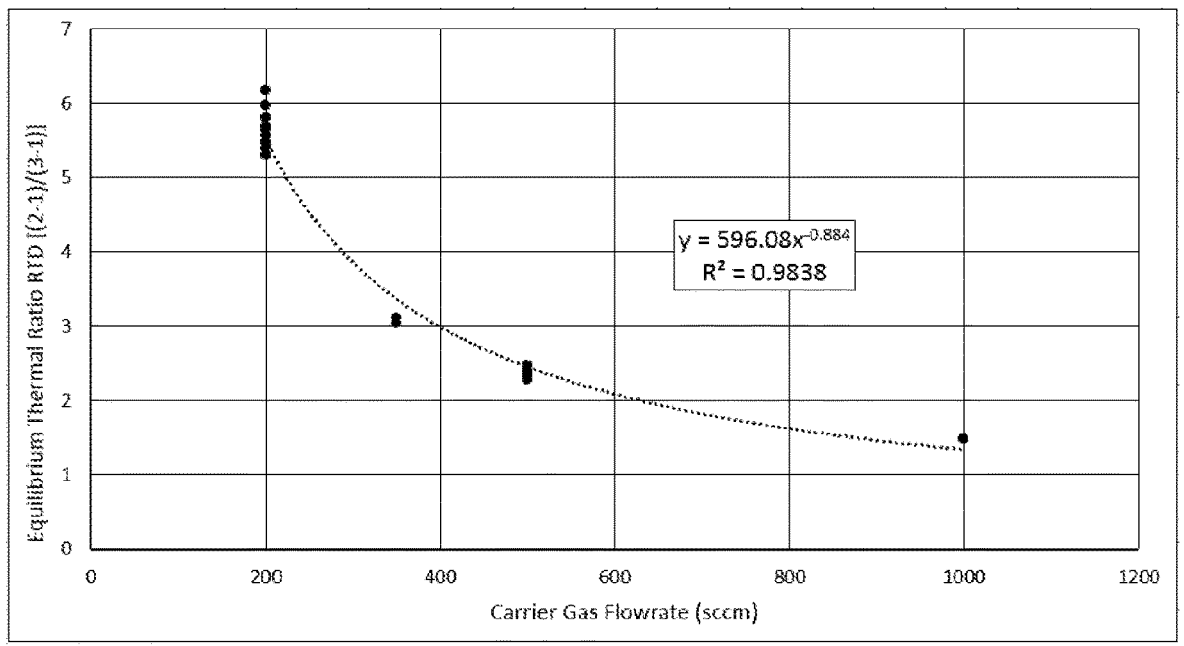
FIG. 7 is a graphical diagram showing thermal absorption of carrier gas vs change in peroxide mass flow rate normalized by temperature change in the gas temperature.

FIG. 7 plots the thermal ratio versus carrier gas flowrate. The grouping of points for each carrier gas flowrate have a wide range of H$_2$O$_2$ mass flowrates (4-18 mg/min). The sensor pressure was kept at 9, 12, 15, and 42 Torr for the carrier gas flowrates of 200, 350, 500, and 1000 sccm, respectively.

The thermal ratio is exponentially dependent on carrier gas flowrate. As carrier gas flowrate approaches zero the pressure of the sensor is <1 Torr. The peroxide vapor mass flowrate ranges from 2.6 to 13.2 sccm (4-20 mg/min). Without carrier gas flow, convective and conductive heat transfer are found to be insignificant and the thermal response of RTD (3-1) was found to be ~0° C. The following thermal ratio limits can be concluded:

$$\lim_{carrier\ flow \to 0} \text{Thermal ratio} = \infty$$

$$\lim_{carrier\ flow \to \infty} \text{Thermal ratio} = 1$$

The thermal ratio can be used to determine the carrier gas flowrate independent of the mass flowrate of peroxide vapor. The equilibrium temperature response of RTD (3-1) or RTD (2-1) can be used to determine the peroxide vapor mass flowrate. With both correlations, the concentration of H$_2$O$_2$ in the gas stream can be approximated without information from the customer.

Effects of Varying Sensor Pressure:

The pressure of the sensor influences the equilibrium temperature of RTD2 and RTD3. At higher sensor pressure, more heat is able to transfer into the carrier gas. This will result in a lower equilibrium Carulite packed bed temperature and greater temperature absorption in the carrier gas. As the fluid pressure increases, the gas becomes denser and the residence time increases. Accordingly, more carrier gas molecules are able to collide with the Carulite to strip off heat.

Figure 8:
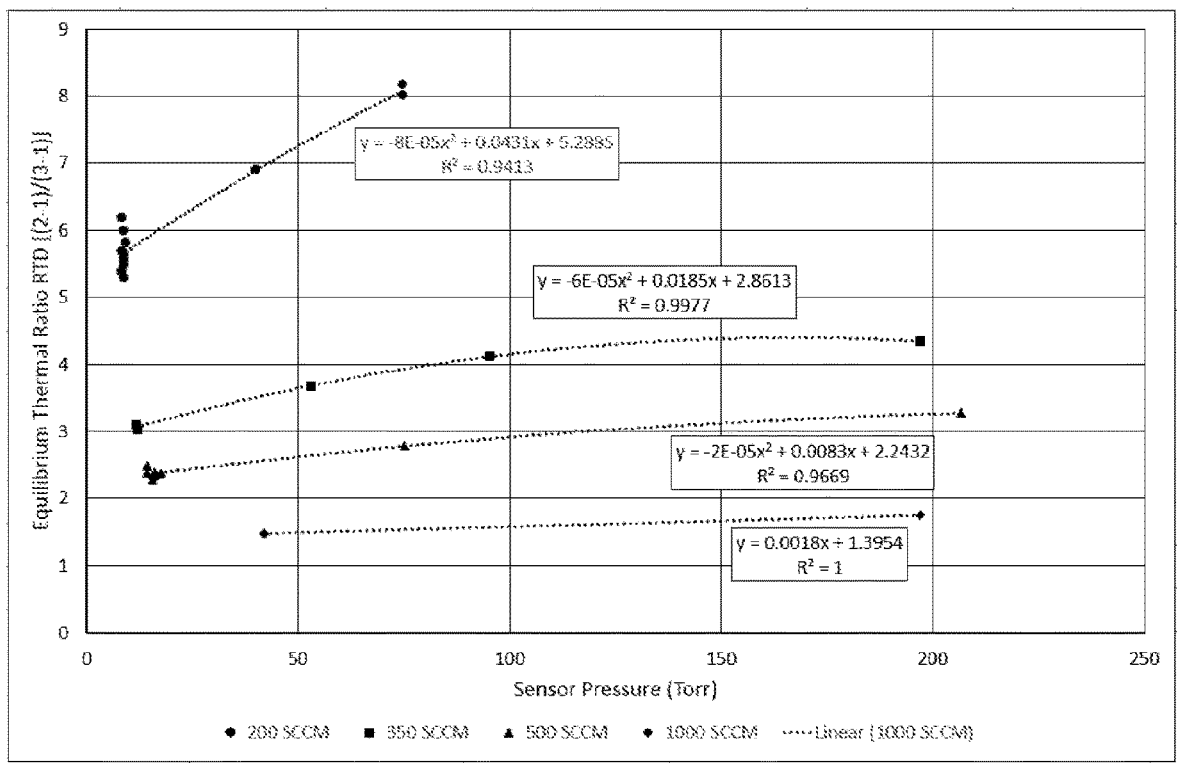
FIG. 8 is a graphical diagram showing thermal absorption of carrier gas vs change in peroxide mass flow rate.

The thermal ratio was evaluated with a sensor pressure range of 10-200 Torr. The equilibrium thermal ratio was found to gradually increase with increasing sensor pressure (FIG. 8). At lower carrier gas flowrates the phenomena is more drastic.

Figure 9:
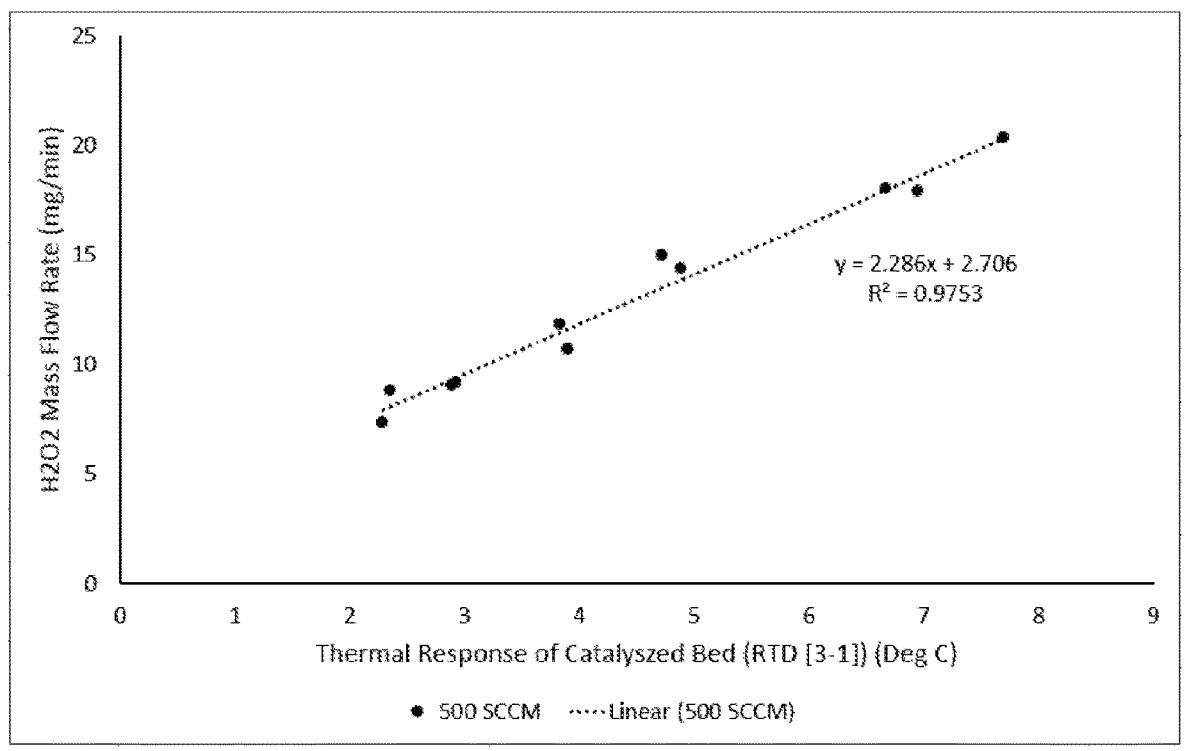
FIG. 9 is a graphical diagram showing thermal absorption of carrier gas vs change in peroxide mass flow rate.

The H$_2$O$_2$ sensor was calibrated at 17 Torr and 500 sccm. The peroxide vapor mass flowrate was varied from 7.33 to 20.3 mg/min (11 points). RTD (3-1) was found to have the best fit (FIG. 9). The following calibration equation was used:

$$\text{Peroxide Vapor } MFR \left(\frac{mg}{min}\right) = 2.286[RTD(3-1)] + 2.706$$

EXAMPLE 2

Figure 10:
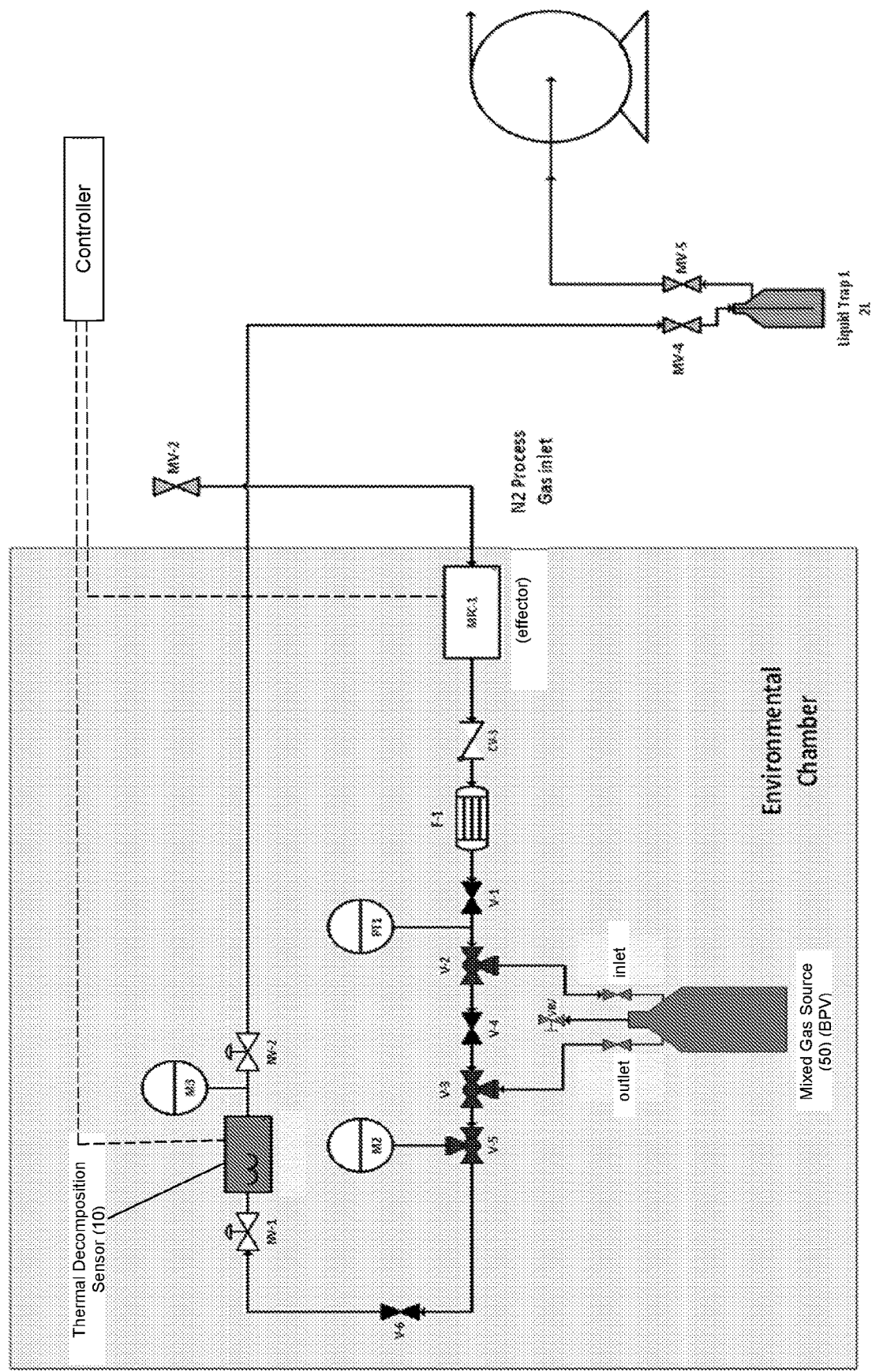
FIG. 10 is a pictorial diagram showing an exemplary experimental P&ID.

FIG. 10 shows the experimental setup for preparing a calibrated sensor that functions at a specified pressure range of H$_2$O$_2$ vapor decomposition. As above, it should be understood that the system shown in FIG. 10 may be used for providing controlled delivery of any of H$_2$O$_2$, hydrazine (H$_2$N$_4$) or ozone with minor modifications thereto. For this experiment, the sensor was run under pressures of 70, 200, 350, and 500 Torr at various BRUTE® Peroxide Vaporizer (BPV) headspace/ampoule pressures at 20° C. The thermal decomposition sensor (10) was installed downstream of NV-1 and upstream M3.

Figure 11:
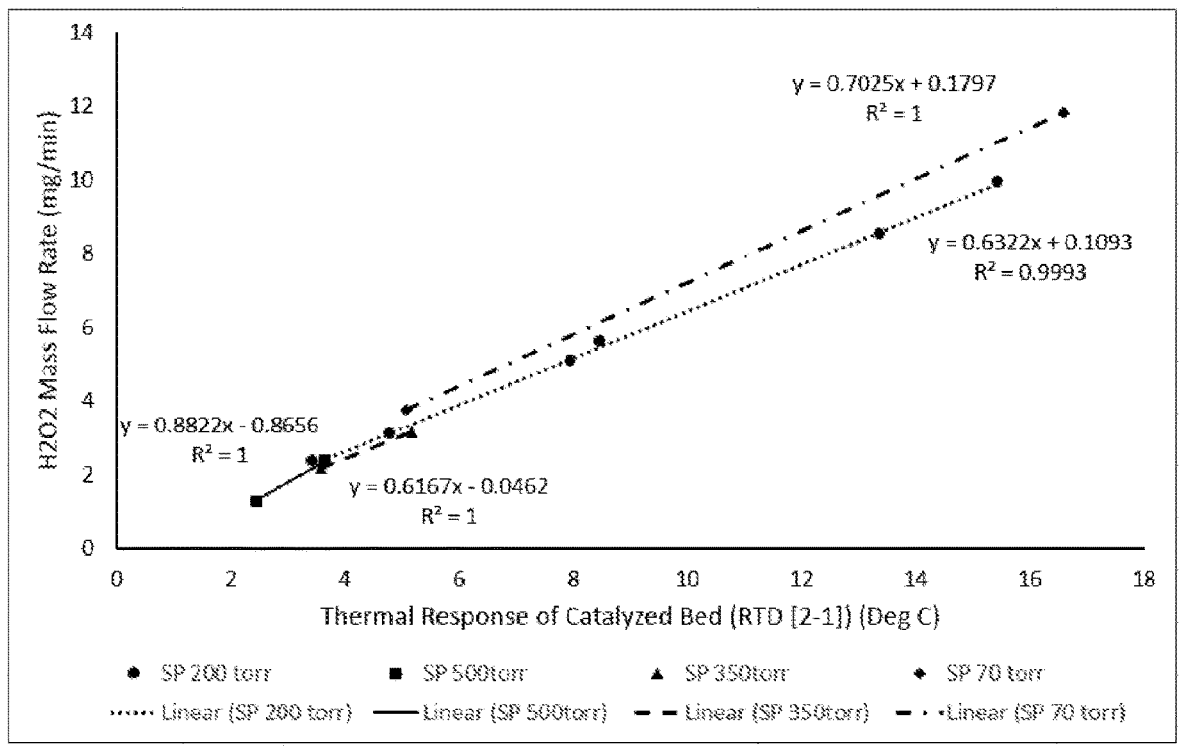
FIG. 11 is a graphical diagram showing hydrogen peroxide mass flow rate as a function of the thermal response of the catalyzed bed at various pressures inside an exemplary sensor.
Figure 12:
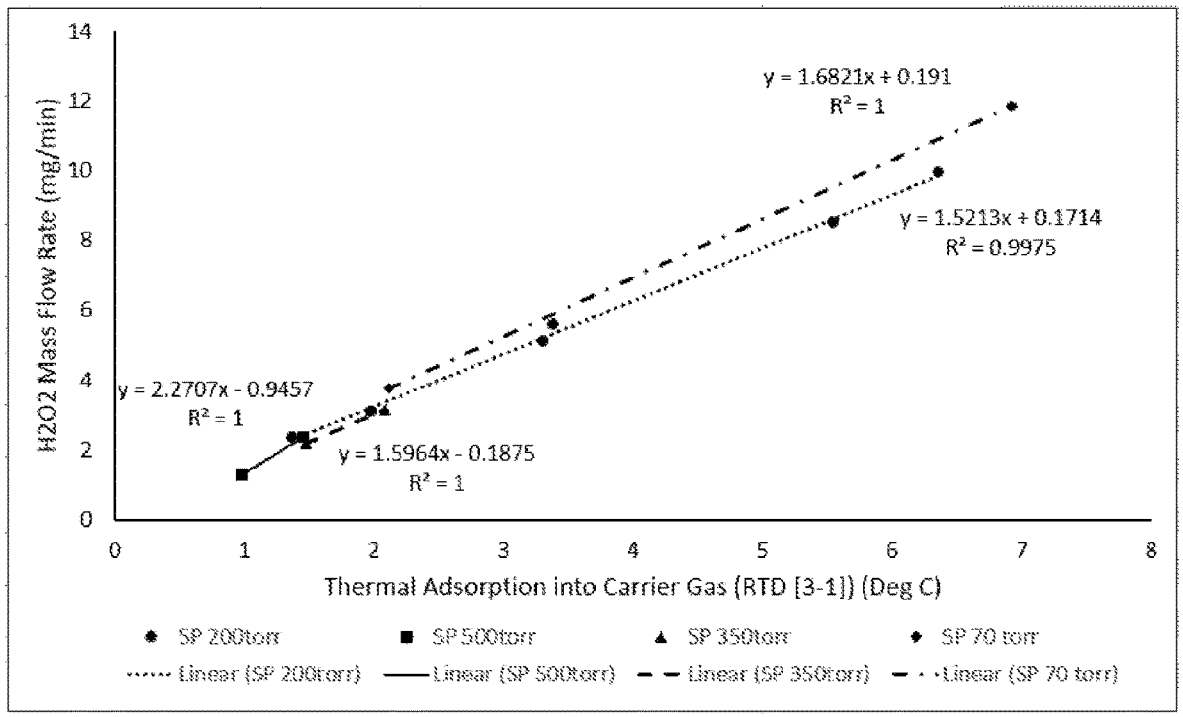
FIG. 12 is a graphical diagram showing hydrogen peroxide mass flow rate as a function of the thermal adsorption of the carrier gas after passing through the catalyzed bed at various pressures inside an exemplary sensor.
Figure 13:
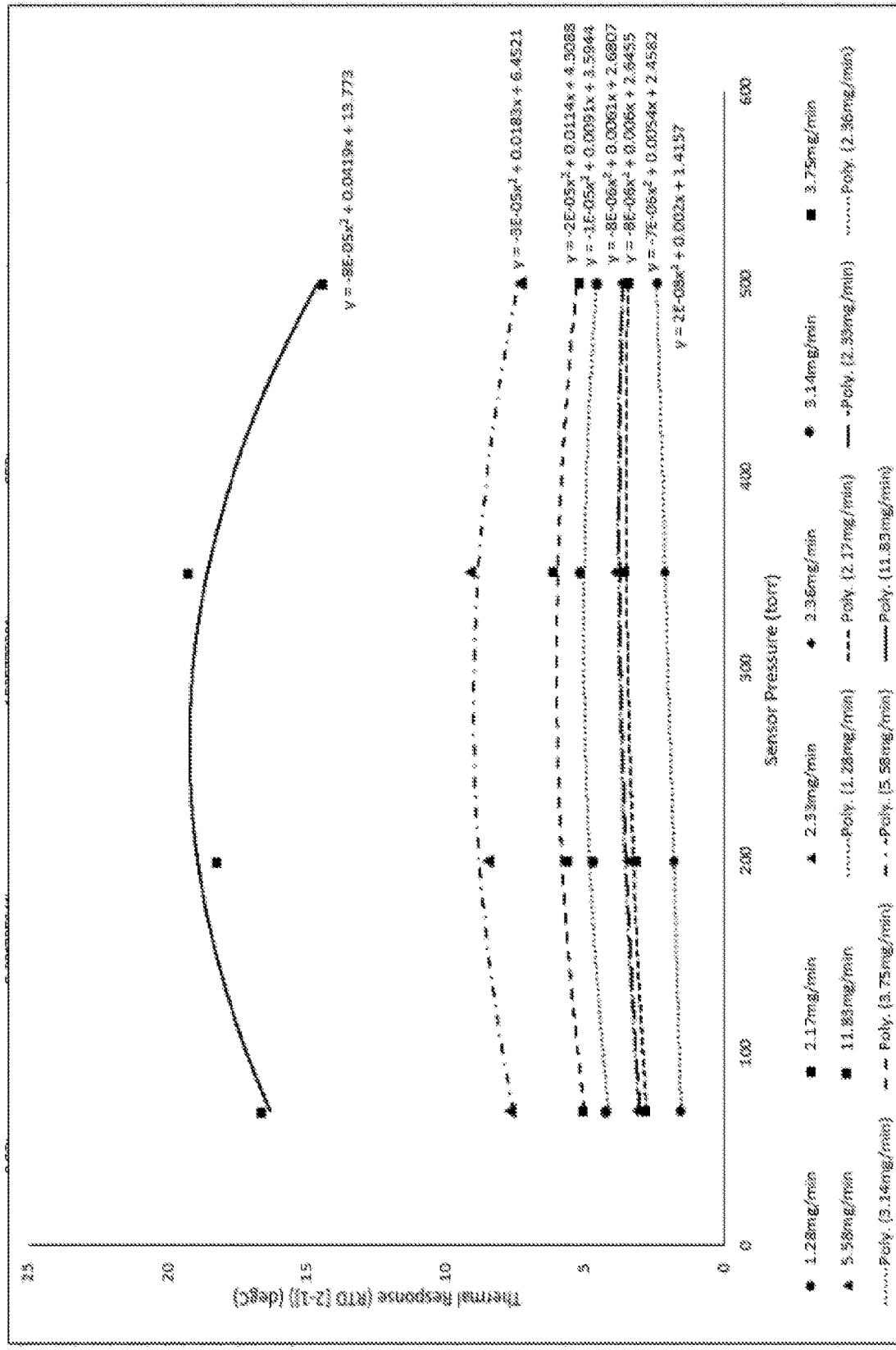
FIG. 13 is a graphical diagram showing the effect of sensor pressure on the thermal response of an exemplary sensor at various hydrogen peroxide flow rates.
Figure 14:
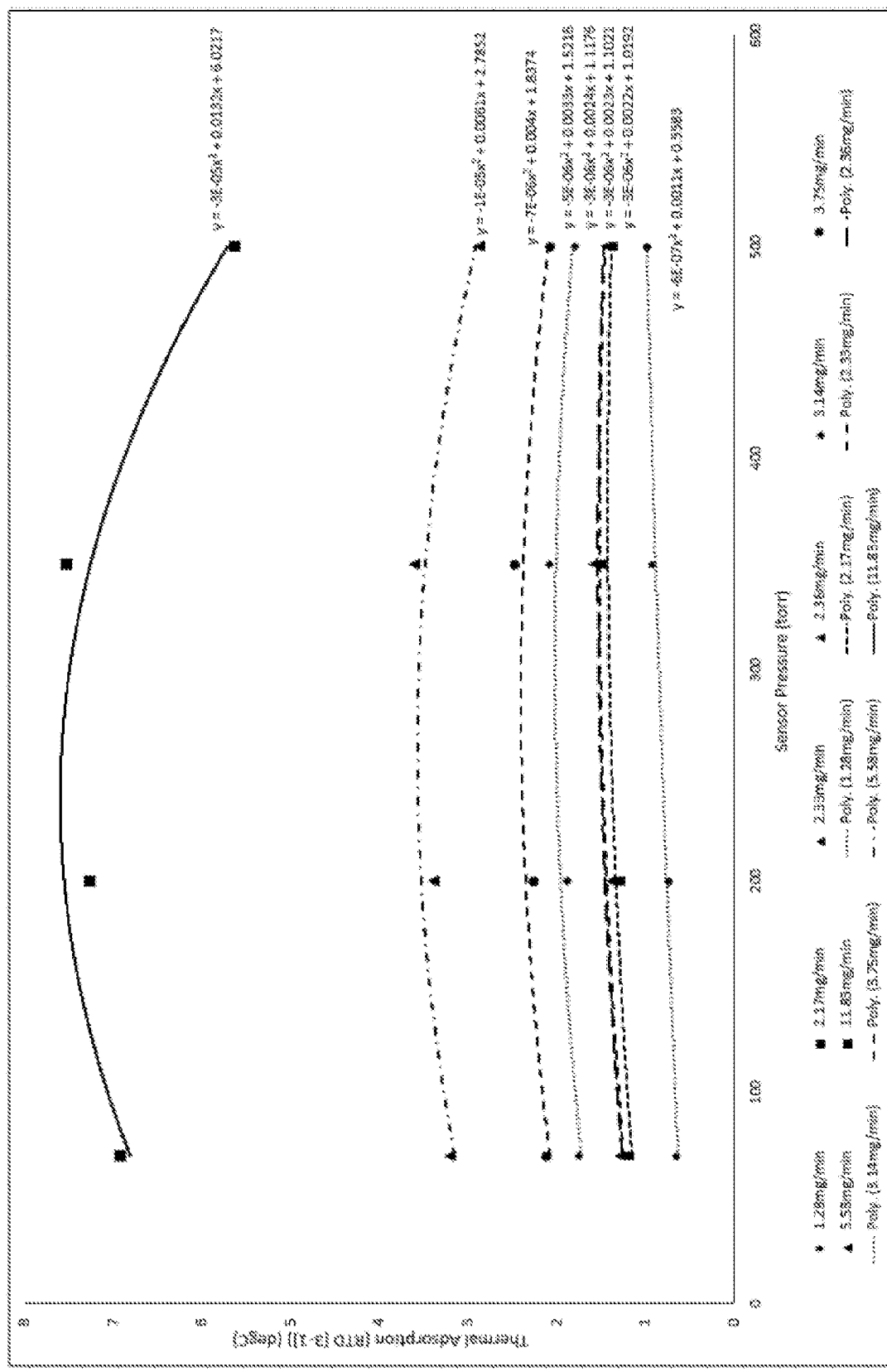
FIG. 14 is a graphical diagram showing the effect of sensor pressure on the thermal adsorption to the carrier gas of an exemplary sensor at various hydrogen peroxide flow rates.

The H$_2$O$_2$ mass flow rate calculated from the change in BPV mass before and after the test are plotted against the thermal response of the packed bed inside the sensor and the thermal adsorption to the carrier gas; the plots are shown in FIGS. 11 and 12, respectively. Both the thermal response and the thermal adsorption showed a positive linear relationship with the mass flow rate of H$_2$O$_2$. Unless otherwise specified, all the experiments were performed at a carrier gas flow rate of 500 sccm at 20° C.

TABLE 2

Mass Flow Rates

| N$_2$ Flowrate (sccm) | H$_2$O$_2$ Mass Flow Rate (mg/min) | H$_2$O$_2$ Mass Flow Rate (mol/min) | H$_2$O$_2$:N$_2$ Vapor Concentration (mol %) |
|---|---|---|---|
| 500 | 19.28 | 0.000567 | 2.54 |
| 500 | 15.38 | 0.000452 | 2.03 |
| 500 | 14.83 | 0.000436 | 1.95 |
| 500 | 14.72 | 0.000433 | 1.94 |
| 500 | 14.44 | 0.000425 | 1.90 |
| 500 | 14.33 | 0.000421 | 1.89 |
| 500 | 13.44 | 0.000395 | 1.77 |
| 500 | 12.11 | 0.000356 | 1.59 |
| 500 | 7.074 | 0.000208 | 0.93 |
| 500 | 3.75 | 0.000110 | 0.49 |

Figure 15:
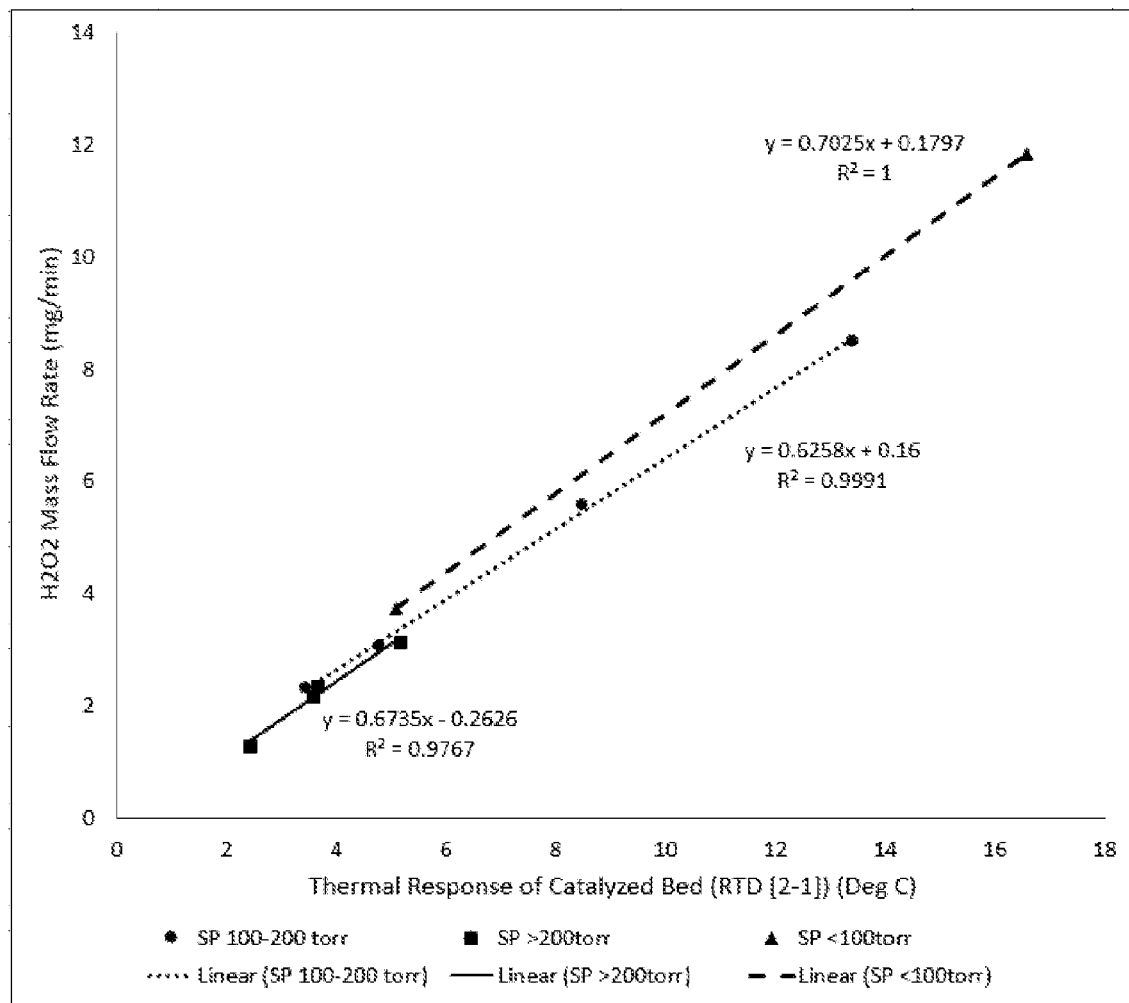
FIG. 15 is a graphical diagram showing exemplary calibration curves generated from the experimental data.
Figure 16:
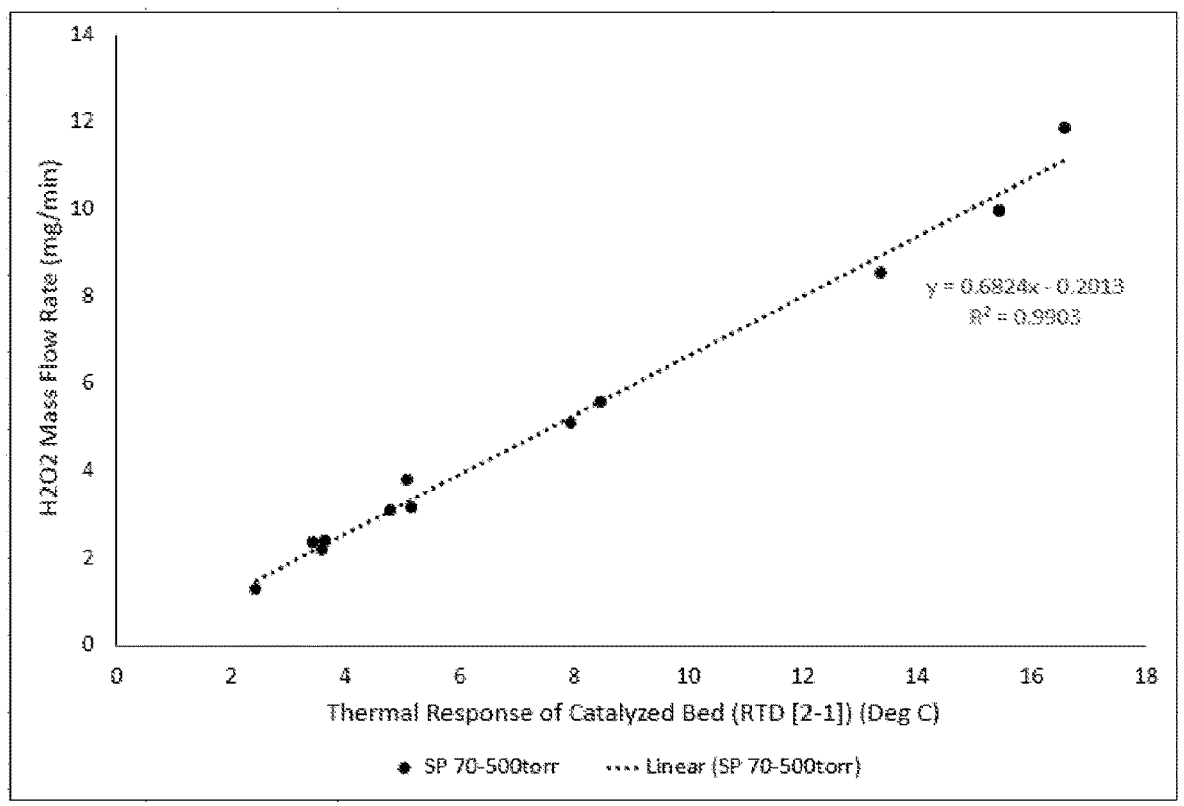
FIG. 16 is a graphical diagram showing a universal calibration curve generated from the experimental data.

Given the effect of sensor pressure, two versions of the calibration curves were experimented; one categorizes the sensor pressure as Low (<100 Torr), Medium (100-200 Torr) and High (>200 Torr) range with a piece-wise function (FIG. 15) while the other is a universal calibration curve that does not correct for the sensor pressure (FIG. 16). The piece-wise calibration has a maximum error of approximately 5% RD while the universal calibration has a maximum error of approximately 14% RD.

Figure 17:
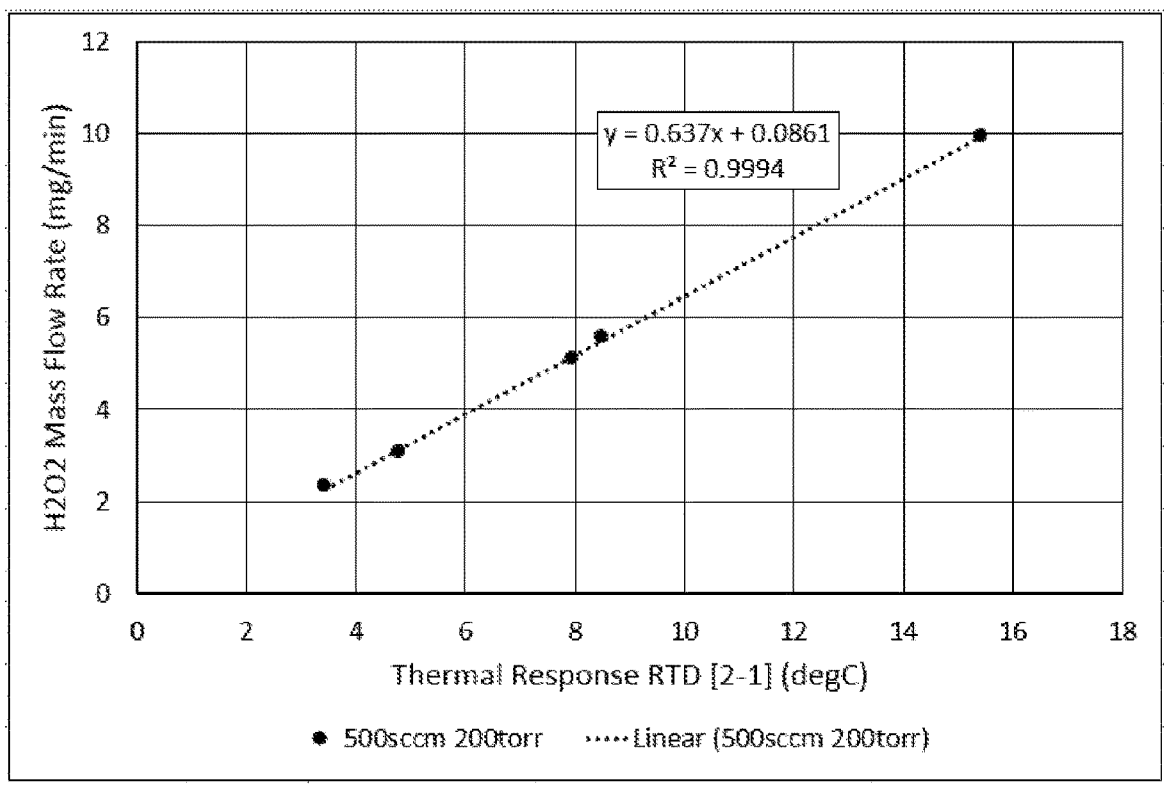
FIG. 17 and FIG. 18 are graphical diagrams demonstrating that temperature of the liquid source can be used to adjust the mass flow rate of a reactive gas.

To prove that the sensor could be used in a closed loop thermal control system, a curve was generated for the BPV at 500 sccm and 20° C. Variable pressures were set in the BPV to generate the curve. Based on the vapor pressure curve for hydrogen peroxide in the BPV, the temperature in the environmental chamber was set to 30° C. and allowed to flow for 4 hours prior to testing to ensure that the temperature is evenly distributed. It should be understood that the environmental chamber contains a heater configured to heat the mixed gas source as described above. The sensor was then run with 500 sccm at 200 Torr with a headspace pressure of 200 Torr. The H$_2$O$_2$ mass flow rate was found to be approximately 9.92 mg/min and the thermal response was approximately 15.44° C. The data was plotted with the points obtained from previous tests at 20° C. under the same operating condition for the sensor in FIGS. 17 and 18. In FIG. 17, the R2 square coefficient was 0.9994 for 30° C. point when added to the 20° C. data set. This demonstrates that for a given set of conditions at the sensor (e.g., pressure and mixed gas stream flow rate), an effector can change either the pressure in the liquid source or the temperature thereof to create a known output of reactive gas.

Figure 18:
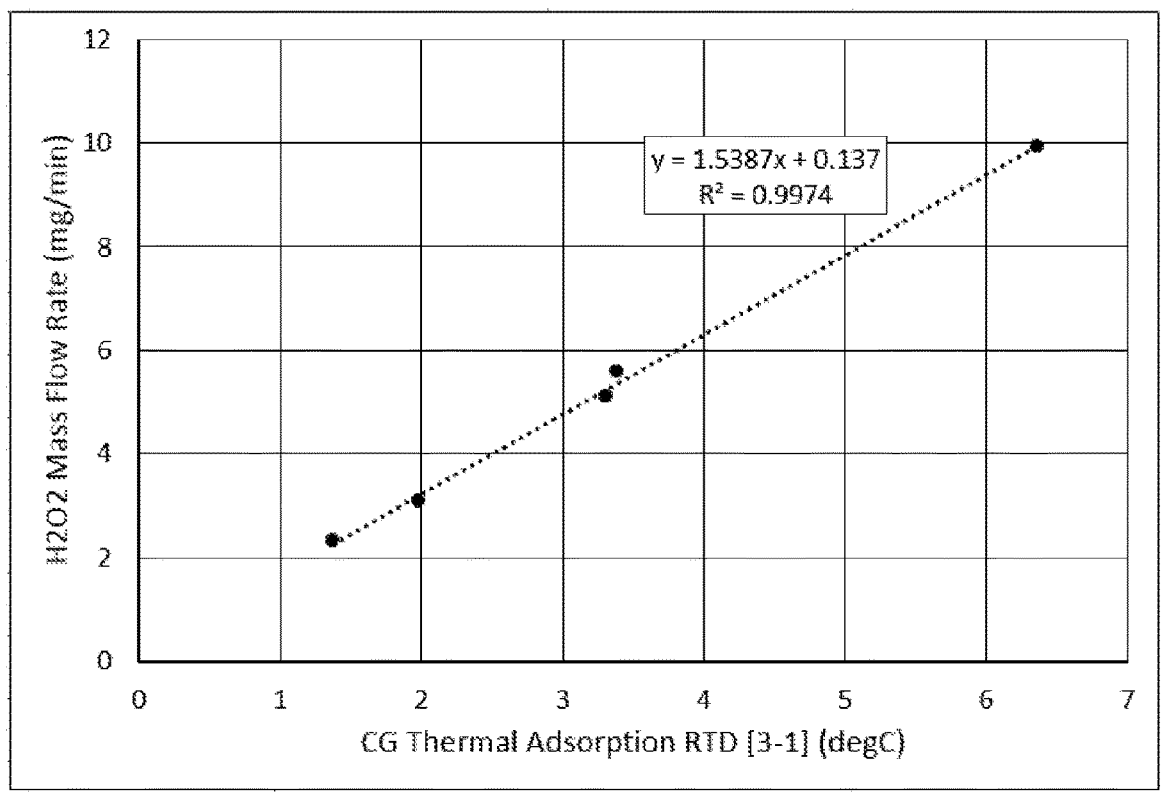

As such, by incorporating the sensor into a catalytically reactive gas delivery loop, the mass of a catalytically reactive gas added to a mixed gas stream can be modulated by raising or lowering temperature or pressure in the liquid source. By generating a calibration curve for a given set of conditions, as shown in FIGS. 17 and 18, an electrical controller can therefore adjust temperature or pressure in a liquid source to generate and measure an expected output for a catalytically reactive gas, such as hydrogen peroxide. For example, if a user needs to deliver 10 mg/min of hydrogen peroxide gas, the BPV temperature can be adjusted to 30° C., which yields a value of 9.92 mg/min. To get closer to 10 mg/min, the temperature may be further adjusted based on the output from the sensor and the calibration curve previously developed. Likewise, the output may be adjusted by holding the temperature fixed and varying the pressure in the BPV headspace.

Accordingly, this example demonstrates that the thermal sensor was able to measure hydrogen peroxide in a carrier gas from 4,900 ppm to 24,800 ppm in the mixed gas flow, as shown in Table 2 (above). As shown in FIG. 16, the sensitivity ranged from 2,200 ppm to 15,600 ppm, or 0.2% to 1.6%.

EXAMPLE 3

In this example, the thermal decomposition sensor was modified with the addition of a Watlow heating rod, thermocouple and thermal switch (Watlow Electric Manufacturing Co., St. Louis, Mo.). The modified sensor was used in combination with a Watlow controller to control the Watlow heater. The sensor was calibrated at a set temperature (controlled via the heater).

Figure 19:
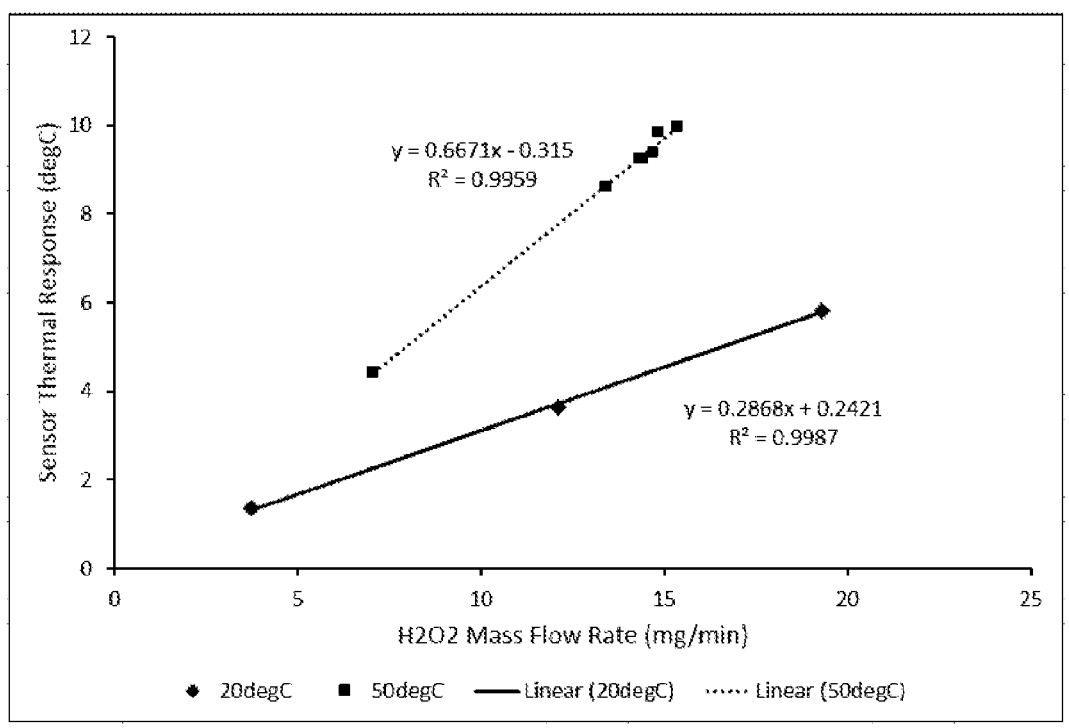
FIG. 19 is a graphical diagram showing sensor thermal response as a function of $H_2O_2$ mass flow rate at different catalyst temperature.

The tests were run inside a 20° C. environmental chamber. The Watlow heater was set to 50° C. and the sensor catalyst was maintained at approximately 46° C. throughout the tests. The thermal response of the thermal decomposition sensor at 20° C. and 50° C. are shown in FIG. 19. As shown, the thermal response increased with increasing sensor/catalyst temperature. As such, it can be observed that the catalytic activity has a positive relationship with the catalyst temperature, which can be expected since the reaction rate has an Arrhenius relationship with temperature. For the same mass flow rate of H$_2$O$_2$, the thermal response changes with changing catalyst temperature.

Although the invention has been described with reference to the above examples, it will be understood that modifications and variations are encompassed within the spirit and scope of the invention. Accordingly, the invention is limited only by the following claims.

What is claimed is:

1. A mass flow control system for controlling mass flow rate of a catalytically reactive gas within a mixed gas stream comprising:
   (a) a mixed gas source providing a mixed gas stream, the mixed gas stream comprising a catalytically reactive gas and a carrier gas, wherein the catalytically reactive gas has a lower molar flow rate than the carrier gas;
   (b) a first sensor comprising a first probe configured to measure a first temperature of the mixed gas stream;
   (c) a decomposition chamber configured to accept a portion of the mixed gas stream, wherein the decomposition chamber comprises a catalyst configured to decompose with the catalytically reactive gas;
   (d) a second sensor comprising a second probe disposed within the decomposition chamber and configured to measure a second temperature of the mixed gas stream following reaction between the catalyst and the catalytically reactive gas;
   (e) a controller in electrical communication with the first and second sensors, wherein the controller is configured to determine the mass flow of the catalytically reactive gas by determining a change in temperature prior to and following contact of the mixed gas stream with the catalyst; and
   (f) an effector in electrical communication with the controller, wherein the effector is configured to change the mass flow rate of the catalytically reactive gas.

2. The mass flow control system of claim 1, wherein the catalytically reactive gas is generated from a liquid source, and wherein the effector is configured to modulate temperature of the liquid source, pressure of a head space of the liquid source, carrier gas flow rate, or any combination thereof.

3. The mass flow control system of claim 1, further comprising a first heater in electrical communication with the controller, wherein the heater is configured to heat the catalyst to a temperature above the dew point of the catalytically reactive gas and a third sensor comprising a third probe disposed at the decomposition chamber and configured to measure a third temperature of the heated catalyst.

4. The mass flow control system of claim 1, wherein the catalyst is selected from the group consisting of silver, platinum, palladium, copper, nickel, manganese oxide, manganese dioxide, copper oxide, and any combination thereof.

5. The mass flow control system of claim 1, wherein the catalytically reactive gas is selected from the group consisting of hydrogen peroxide gas and hydrazine ($H_2N_4$).

6. The mass flow control system of claim 2, wherein the liquid source is selected from the group consisting of anhydrous hydrogen peroxide and anhydrous hydrazine.

7. The mass flow control system of claim 1, wherein the carrier gas is selected from the group consisting of nitrogen, hydrogen, argon, helium, steam, clean dry air, oxygen, $NH_3$, carbon dioxide and any combination thereof.

8. The mass flow control system of claim 1, wherein the mixed gas stream is provided at a pressure of about 10 Torr to 2 barg.

9. The mass flow control system of claim 2, wherein the effector is selected from the group consisting of a pressure regulating valve disposed upstream of the liquid source, a pressure regulating valve disposed downstream of the liquid source, a heater configured to regulate temperature of the liquid source, and a chiller configured to regulate temperature of the liquid source.

10. The mass flow control system of claim 1, wherein the concentration of the catalytically reactive gas delivered by the system is about 100 parts per million (ppm) to 100,000 ppm.

11. The mass flow control system of claim 1, wherein, when operating under a vacuum, the pressure of the mixed gas stream provided to the system is about 10.0 to 100.0 Torr.

12. The mass flow control system of claim 1, wherein the temperature of the catalytically reactive gas delivered to the system is about 15° C. to 80° C.

13. The mass flow control system of claim 1, wherein the change in temperature is approximately proportional with the change in catalytically reactive gas mass flow rate, and wherein the change in temperature is relatively independent of the pressure or flow rate of the mixed gas stream.

14. The mass flow control system of claim 1, wherein the carrier gas flow rate is held constant.

15. The mass flow control system of claim 1, wherein the first sensor, second sensor and decomposition chamber are disposed within a housing, the housing comprising:
(a) an inlet;
(b) a first tube configured to provide fluid communication between the inlet and the decomposition chamber;
(c) an outlet; and
(d) a second tube configured to provide fluid communication between the decomposition chamber and the outlet,
wherein the first sensor is disposed within the first tube.

16. The mass flow control system of claim 15, wherein the second sensor is disposed within the decomposition chamber.

17. The mass flow control system of claim 3, further comprising a second heater configured to heat the mixed gas stream prior to entering the decomposition chamber.

18. The mass flow control system of claim 15, wherein the housing further comprises a first heater disposed in contact with the decomposition chamber and configured to heat the catalyst to a temperature above the dew point of the catalytically reactive gas, and a third sensor comprising a third probe disposed at the decomposition chamber and configured to measure a third temperature of the catalyst.

19. The mass flow control system of claim 1, wherein the mixed gas stream is provided at about 15° C. to 150° C.

20. A method of controlling mass flow of a dilute catalytically reactive gas in a mixed gas stream comprising:
(a) providing a mixed gas stream from a mixed gas source, the mixed gas stream comprising a dilute catalytically reactive gas generated from a liquid source, and a carrier gas;
(b) determining a first temperature of the mixed gas stream;
(c) exposing at least a portion of the mixed gas stream to a catalyst configured to react with the catalytically reactive gas;
(d) determining a second temperature of the mixed gas stream following reaction between the catalyst and the catalytically reactive gas;
(e) determining mass flow of the catalytically reactive gas by determining a change in temperature following contact of the mixed gas stream with the catalyst, wherein the change in temperature is relatively independent of the pressure or flow rate of the mixed gas stream; and
(f) adjusting one or more of temperature of the liquid source, pressure of a headspace of the liquid source, and carrier gas flow rate to achieve a desired mass flow rate of the dilute catalytically reactive gas.

21. The method of claim 20, wherein the step of adjusting is accomplished using an effector selected from the group consisting of a pressure regulating valve disposed upstream of the liquid source, a pressure regulating valve disposed downstream of the liquid source, a heater configured to regulate temperature of the liquid source, and a chiller configured to regulate temperature of the liquid source.

22. The method of claim 20, wherein the catalyst is selected from the group consisting of silver, platinum, palladium, copper, nickel, manganese oxide, manganese dioxide, copper oxide, and any combination thereof.

23. The method of claim 20, wherein the catalytically reactive gas is selected from the group consisting of hydrogen peroxide gas and $H_2N_4$.

24. The method of claim 20, wherein the carrier gas is selected from the group consisting of nitrogen, hydrogen, argon, helium, steam, clean dry air, oxygen, $NH_3$, carbon dioxide, and any combination thereof.

25. The method of claim 20, further comprising heating the catalyst to a temperature above the dew point of the catalytically reactive gas prior to exposing to the mixed gas stream.

26. The method of claim 25, further comprising heating the mixed gas stream prior to exposing to the catalyst.

27. The method of claim 20, wherein the mixed gas stream is provided at about 0.076 Torr to 800 Torr.

28. The method of claim 20, further comprising repeating steps (d)-(f) after the step of adjusting to achieve a desired mass flow rate of the dilute catalytically reactive gas.

29. The method of claim 20, wherein the mixed gas stream is provided at about 15° C. to 150° C.

30. The method of claim 20, wherein the concentration of the dilute catalytically reactive gas in the mixed gas stream is about 500 ppm to about 25,000 ppm.

31. The mass flow control system of claim 1, wherein the catalytically reactive gas comprises ozone generated from an ozone generator, and wherein the effector is selected from the group consisting of a thermal mass flow controller disposed upstream of the ozone generator and a power supply configured to deliver power to the ozone generator.

* * * * *